United States Patent
Shiota et al.

(10) Patent No.: US 10,059,662 B2
(45) Date of Patent: Aug. 28, 2018

(54) SULFONIUM SALT, PHOTOACID GENERATOR, AND PHOTOSENSITIVE COMPOSITION

(71) Applicant: TOKYO OHKA KOGYO CO., LTD., Kawasaki-shi (JP)

(72) Inventors: Dai Shiota, Kawasaki (JP); Kunihiro Noda, Kawasaki (JP); Hiroki Chisaka, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/506,680

(22) PCT Filed: Sep. 25, 2015

(86) PCT No.: PCT/JP2015/077196
§ 371 (c)(1),
(2) Date: Feb. 24, 2017

(87) PCT Pub. No.: WO2016/047784
PCT Pub. Date: Mar. 31, 2016

(65) Prior Publication Data
US 2017/0305848 A1   Oct. 26, 2017

(30) Foreign Application Priority Data
Sep. 26, 2014  (JP) .................................. 2014-197335

(51) Int. Cl.
*G03F 7/004* (2006.01)
*C07C 381/12* (2006.01)
(Continued)

(52) U.S. Cl.
CPC .......... *C07C 381/12* (2013.01); *C07C 309/06* (2013.01); *C09K 3/00* (2013.01);
(Continued)

(58) Field of Classification Search
CPC ...... G03F 7/004; G03F 7/0045; G03F 7/0046; G03F 7/322; G03F 7/2004; G03F 7/039; C07C 381/12; C07C 309/06
(Continued)

(56) References Cited

U.S. PATENT DOCUMENTS 3,981,897 A   9/1976   Crivello
4,704,324 A   11/1987  Davis et al.
(Continued)

FOREIGN PATENT DOCUMENTS

CN   1243122 A    2/2000
EP   0972761 A1   7/1999
(Continued)

OTHER PUBLICATIONS

STN Caplus, Jan. 14, 1997 (Jan. 14, 1997), XP002117759.
(Continued)

*Primary Examiner* — Amanda C Walke
(74) *Attorney, Agent, or Firm* — Knobbe Martens Olson & Bear LLP

(57) ABSTRACT

A novel sulfonium salt having high sensitivity with respect to active energy rays, a photoacid generator including the sulfonium salt, and a photosensitive composition containing the photoacid generator. The sulfonium salt is represented by formula (a1). In the formula, $R^1$ and $R^2$ each independently represent the group that is represented by formula (a2) or an alkyl group that may be substituted by a halogen atom, $R^1$ and $R^2$ are bonded to each other and may form a ring with the sulfur atom within the formula, $R^3$ is the group represented by formula (a3) or the group represented by formula (a4), $A^1$ represents S or the like, $X^-$ represents a monovalent anion, and $R^1$ and $R^2$ are not both an alkyl group which may be substituted with a halogen atom. In formulas (a2) to (a4),
(Continued)

the ring $Z^1$ represents an aromatic hydrocarbon ring, $R^4$, $R^6$, $R^9$, and $R^{10}$ each represents a specific monovalent group, $R^5$, $R^7$, and $R^8$ each represents a specific divalent group, $A^2$ and $A^3$ each represents S or the like, m1 represents an integer of 0 or more, and n1 and n2 each represent 0 or more.

(a1)

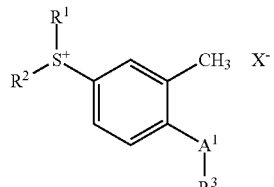

(a2)

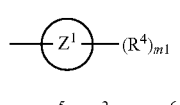

(a3)

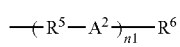

(a4)

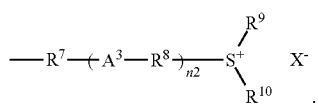

4 Claims, 4 Drawing Sheets

(51) Int. Cl.
  *C07C 309/06* (2006.01)
  *C09K 3/00* (2006.01)
  *G03F 7/038* (2006.01)
  *G03F 7/039* (2006.01)
  *G03F 7/20* (2006.01)
  *G03F 7/32* (2006.01)

(52) U.S. Cl.
  CPC .......... *G03F 7/0045* (2013.01); *G03F 7/0046* (2013.01); *G03F 7/039* (2013.01); *G03F 7/0382* (2013.01); *G03F 7/0392* (2013.01); *G03F 7/0397* (2013.01); *G03F 7/2004* (2013.01); *G03F 7/322* (2013.01)

(58) Field of Classification Search
  USPC .................. 430/270.1, 322, 913; 568/18
  See application file for complete search history.

(56) References Cited

U.S. PATENT DOCUMENTS

| | | | |
|---|---|---|---|
| 5,012,001 A | 4/1991 | Crivello | |
| 6,093,753 A | 7/2000 | Takahashi | |
| 6,111,143 A * | 8/2000 | Park | C07C 381/12 568/18 |
| 6,723,483 B1 | 4/2004 | Oono et al. | |
| 8,617,787 B2 * | 12/2013 | Suzuki | C07C 381/12 430/270.1 |
| 8,932,797 B2 * | 1/2015 | Thackeray | G03F 7/0045 430/270.1 |
| 2002/0090569 A1 | 7/2002 | Suzuki et al. | |
| 2004/0005301 A1 * | 1/2004 | Goldman | C12N 5/0678 424/93.21 |
| 2005/0148679 A1 * | 7/2005 | Chiu | C07C 381/12 522/6 |
| 2008/0311522 A1 | 12/2008 | Iwai et al. | |
| 2010/0248135 A1 * | 9/2010 | Masuyama | G03F 7/0046 430/270.1 |
| 2011/0192639 A1 * | 8/2011 | Shinya | C07C 381/12 174/259 |
| 2011/0300482 A1 | 12/2011 | Suzuki et al. | |
| 2011/0300484 A1 * | 12/2011 | Yamato | C07C 317/04 430/281.1 |
| 2015/0037734 A1 * | 2/2015 | Nagamine | C07C 381/12 430/281.1 |

FOREIGN PATENT DOCUMENTS

| | | |
|---|---|---|
| EP | 0972761 A1 | 1/2000 |
| EP | 1113005 A1 | 7/2001 |
| JP | S50-151997 | 12/1975 |
| JP | S61-100557 | 5/1986 |
| JP | S62-502320 | 9/1987 |
| JP | H02-178303 | 7/1990 |
| JP | H08-165290 | 6/1996 |
| JP | H09-118663 | 5/1997 |
| JP | 2000-044535 | 2/2000 |
| JP | 2002-193925 | 7/2002 |
| JP | 2010-121078 A | 6/2010 |
| JP | 2010-215616 | 9/2010 |
| JP | 2011-039411 A | 2/2011 |
| JP | 2011-102269 | 5/2011 |
| JP | 2012-027290 A | 2/2012 |
| JP | 2013-043864 | 3/2013 |
| WO | WO 2014/033967 A1 | 3/2014 |

OTHER PUBLICATIONS

Extended European search report in European Patent Application No. 15843379.7, dated Aug. 29, 2017.
Asakura T., et al., PAG study in EUV lithography, Journal of Photopolymer Science and Technology, 2009, V.22, p. 89-95, p. 89, Table 1-3, Figure 1-6.
Kunza A., et al., Triplet quenching by onium salts in polar and nonpolar solvents, Journal of Photochemistry and Photobiology A:Chemistry, 1997, V.110, p. 115-122, Scheme 1, 2, Table 2,3.
Mace Y., et al., Self-Immolative Reduction of Trifluoromethyl Sulfoxides Promoted by Trifluoromethanesulfonic Anhydride, European Jounal of Organic Chemistry, 2010, p. 5772-5776, p. 5773, compound 5b.
Zhang B., et al., Tertiary sulfonium as a cationic functional group for hyroxide exchange membranes, RSC Advances, 2012, V.2, p. 12683-12685, p. 12684, Scheme 1.
Office Action in Chinese Patent Application No. 201580050973.9, dated May 28, 2018.

* cited by examiner

[FIG. 1]
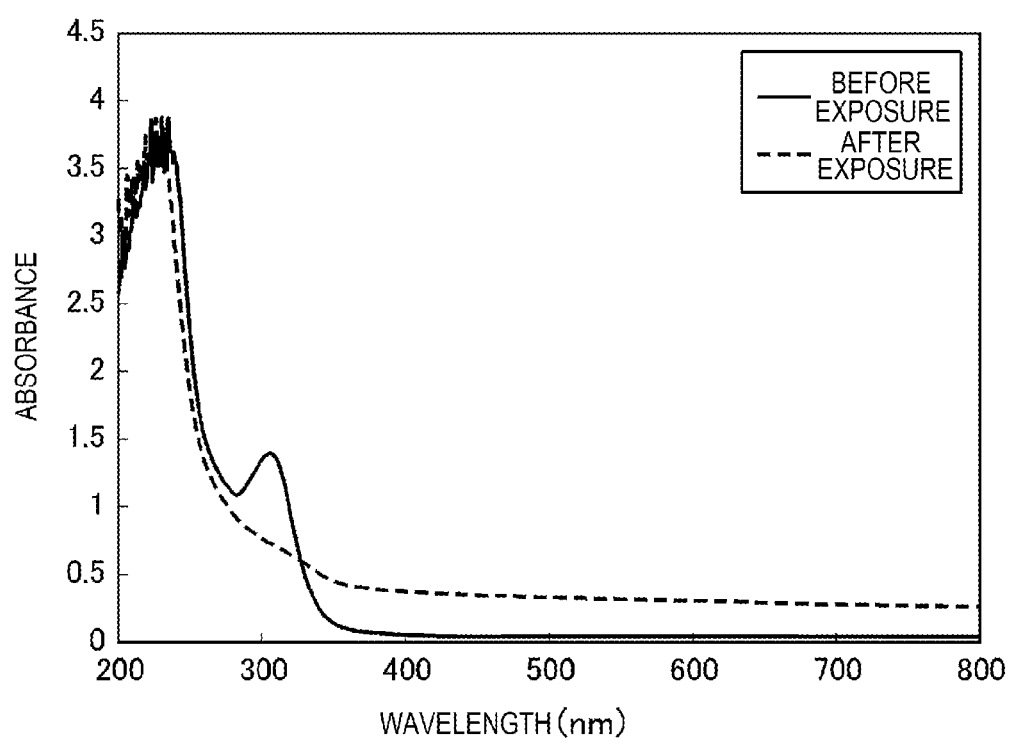

[FIG. 2]
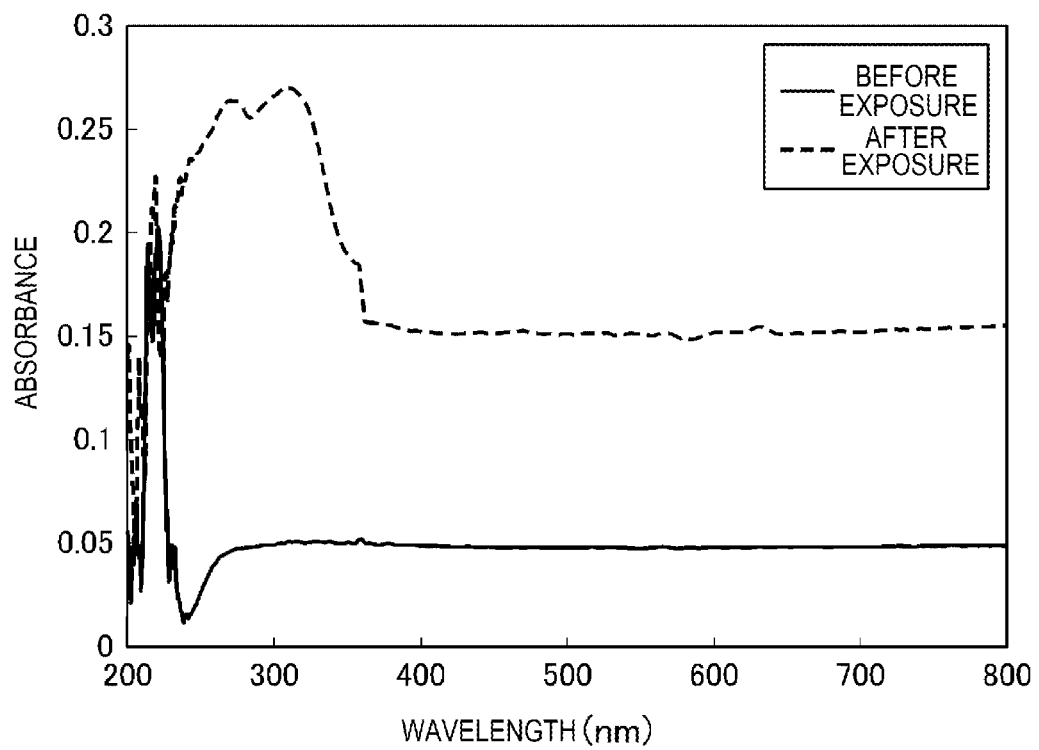

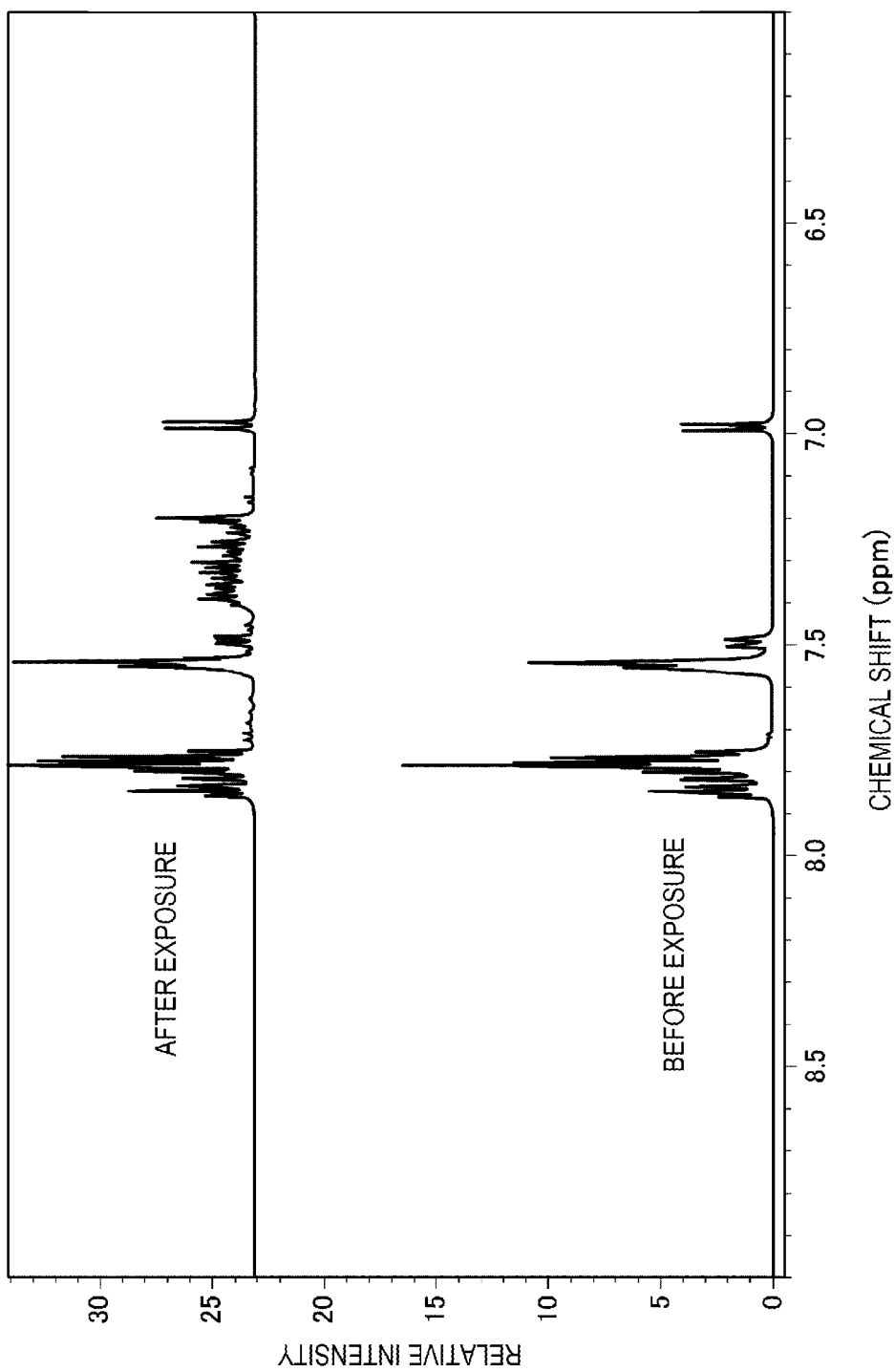
[FIG. 3]

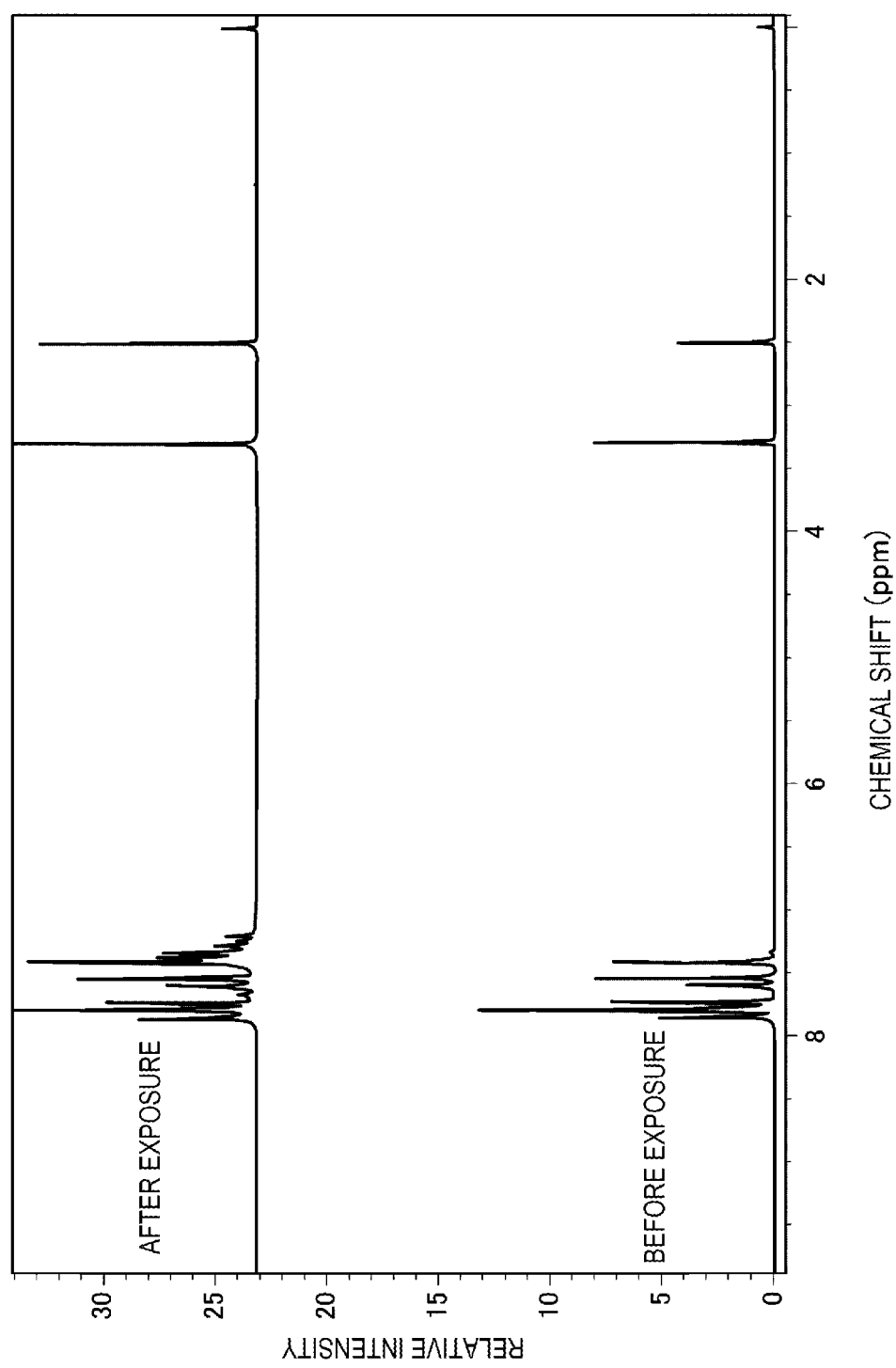
[FIG. 4]

SULFONIUM SALT, PHOTOACID GENERATOR, AND PHOTOSENSITIVE COMPOSITION

This application is the U.S. National Phase under 35 U.S.C. § 371 of International Application PCT/JP2015/077196, filed Sep. 25, 2015, designating the U.S., and published in Japanese as WO 2016/047784 on Mar. 31, 2016, which claims priority to Japanese Patent Application No. 2014-197335, filed Sep. 26, 2014, the entire contents of which are incorporated herein by reference.

TECHNICAL FIELD

The present invention relates to a sulfonium salt, a photoacid generator, and a photosensitive composition. More particularly, the present invention relates to a sulfonium salt suitable for curing a cationically polymerizable compound under the action of active energy rays such as light, electronic beams or X-rays, a photoacid generator including the sulfonium salt and a photosensitive composition containing the photoacid generator.

BACKGROUND ART

A triarylsulfonim salt (PTL 1), a phenacylsulfonium salt having a naphthalene skeleton (PTL 2), a dialkylbenzylsulfonium salt (PTL 3), a sulfonium salt having a thioxanthone skeleton introduced therein (PTL 4) and a sulfonium salt having a polyaryl sulfide skeleton (PTL 5) are conventionally known as a photoacid generator used in curing a cationically polymerizable compound such as an epoxy compound under the action of active energy rays such as light, electronic beams or X-rays.

CITATION LIST

Patent Literature

[PTL 1] Japanese Unexamined Patent Application, Publication No. S50-151997
[PTL 2] Japanese Unexamined Patent Application, Publication No. H9-118663
[PTL 3] Japanese Unexamined Patent Application, Publication No. H2-178303
[PTL 4] Japanese Unexamined Patent Application, Publication No. H8-165290
[PTL 5] Japanese Unexamined Patent Application, Publication No. S61-100557

SUMMARY OF THE INVENTION

Technical Problem

The conventional sulfonium salt has a problem that the sensitivity to active energy rays is not sufficient. Example of the conventional sulfonium salt includes a sulfonium salt represented by the following formula (z1) (hereinafter referred to as sulfonium salt (z1)). The sulfonium salt (z1) produces an acid when irradiated with ultraviolet rays. According to the investigations by the present inventors, it was found that when the sulfonium salt (z1) is irradiated with ultraviolet rays, an acid is produced, and additionally a by-product having absorption in an ultraviolet region is produced. The by-product absorbs ultraviolet rays in the co-presence of the sulfonium salt (z1) and the by-product, and ultraviolet rays reaching the sulfonium salt (z1) are decreased. As a result, it is presumed that the sulfonium salt (z1) is difficult to enhance the sensitivity to ultraviolet rays.

[Chemical formula 1]

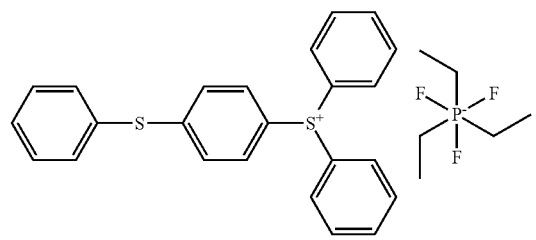

The present invention has been made in view of the above situations, and has an object to provide a novel sulfonium salt having high sensitivity to active energy rays, a photoacid generator including the sulfonium salt, and a photosensitive composition containing the photoacid generator.

Solution to Problem

The present inventors made extensive and intensive investigations to solve the above problems. As a result, they have found that a sulfonium salt having a methyl group at a specific position enhances the sensitivity to active energy rays, and have reached to complete the present invention. Specifically, the present invention provides the following inventions.

A first aspect of the present invention is a sulfonium salt represented by the following general formula (a1):

[Chemical formula 2]

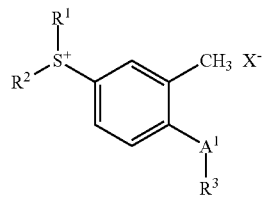

wherein $R^1$ and $R^2$ independently represent an alkyl group which may be substituted with a halogen atom or a group represented by the following general formula (a2), $R^1$ and $R^2$ may be combined to form a ring together with the sulfur atom in the formula, $R^3$ represents a group represented by the following general formula (3a) or a group represented by the following general formula (4a), $A^1$ represents S, O or Se, and $X^-$ represents a monovalent anion, provided that $R^1$ and $R^2$ are not simultaneously an alkyl group which may be substituted with a halogen atom;

[Chemical formula 3]

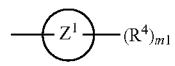

wherein a ring $Z^1$ represents an aromatic hydrocarbon ring, $R^4$ represents an alkyl group which may be substituted with a halogen atom; a hydroxy group, an alkoxy group, an alkylcarbonyl group, an alkoxycarbonyl group, an acyloxy group, an alkylthio group, a thienyl group, a thienylcarbonyl group a furanyl group, a furanylcarbonyl group, a selenophenyl group, a selenophenylcarbonyl group, a heterocyclic aliphatic hydrocarbon group, an alkylsulfinyl group, an alkylsulfonyl group, a hydroxy(poly)alkyleneoxy group, an amino group which may be substituted, a cyano group, a nitro group or a halogen atom, and m1 is an integer of 0 or more;

[Chemical formula 4]

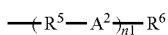
(a3)

wherein $R^5$ represents an alkylene group which may be substituted with a hydroxy group, an alkoxy group, an alkyl carbonyl group, an aryl carbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, or a group represented by the following general formula (a5), $R^6$ represents an alkyl group which may be substituted with a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, or a group represented by the following general formula (a6), $A^2$ represents a single bond, S, O, a sulfinyl group or a carbonyl group, and n1 is 0 or 1;

[Chemical formula 5]

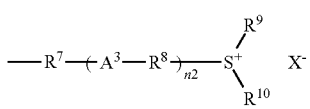
(a4)

wherein $R^7$ and $R^8$ independently represent an alkylene group which may be substituted with a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, or a group represented by the following general formula (a5), $R^9$ and $R^{10}$ independently represent an alkyl group which may be substituted with a halogen atom, or a group represented by the general formula (a2), $R^9$ and $R^{10}$ may be combined to form a ring together with the sulfur atom in the formula, $A^3$ represents a single bond, S, O, a sulfinyl group or a carbonyl group, $X^-$ is the same as defined above, and n2 is 0 or 1, provided that $R^9$ and $R^{10}$ are not simultaneously an alkyl group which may be substituted with a halogen atom;

[Chemical formula 6]

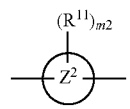
(a5)

wherein a ring $Z^2$ represents an aromatic hydrocarbon ring, $R^{11}$ represents an alkyl group which may be substituted with a halogen atom, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, and m2 is an integer of 0 or more;

[Chemical formula 7]

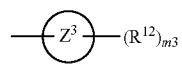
(a6)

wherein a ring $Z^3$ represents an aromatic hydrocarbon ring, $R^{12}$ represents an alkyl group which may be substituted with a halogen atom, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, a thienylcarbonyl group, a furanylcarbonyl group, a selenophenylcarbonyl group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, and m3 is an integer of 0 or more.

A second aspect of the present invention is a photoacid generator including the sulfonium salt according to the first aspect of the present invention.

A third aspect of the present invention is a photosensitive composition containing the photoacid generator including the sulfonium salt according to the first aspect of the present invention.

Advantageous Effects of Invention

According to the present invention, a novel sulfonium salt having high sensitivity to active energy rays, a photoacid generator including the sulfonium salt, and a photosensitive composition containing the photoacid generator can be provided.

The sulfonium salt of the present invention has excellent curability by the action of active energy rays, particularly ultraviolet rays, when used as a photoacid generator in curing a cationically polymerizable compound, and can cure the cationically polymerizable compound even though a sensitizer is not used. The sulfonium salt of the present invention also has excellent thick film curability.

The photosensitive composition of the present invention contains the sulfonium salt of the present invention. Therefore, when the photosensitive composition contains a cationically polymerizable compound, such a photosensitive composition can be cured with ultraviolet rays. Furthermore, the photosensitive composition of the present invention has high storage stability and is not required to use a sensitizer. Therefore, the photosensitive composition is excellent in costs and workability.

When the photosensitive composition of the present invention contains a cationically polymerizable compound, its cured product can be obtained without using a sensitizer. As a result, the photosensitive composition is free from the problems of coloration and deterioration due to residual sensitizer.

In view of the above, the sulfonium salt of the present invention is suitable for use as a photoacid generator used in a paint, a coating material, an ink, an ink-jet ink, a positive-type resist (connection terminals or wiring pattern formation in the production of electronic parts such as a circuit substrate, CSP and MEMS element), a resist film, a liquid resist, a negative-type resist (a permanent film material of a surface protective film, an interlayer insulation film, a flattened film or the like of a semiconductor element and the like), an MEMS resist, a photosensitive material, various adhesives, a molding material, a casting material, a putty, a glass fiber impregnant, a filler, a sealing material, an encapsulant, an optical semiconductor (LED) encapsulant, a nanoimprint material, an optical waveguide material, an optical shaping and micro-optical shaping material, and the like. Furthermore, when the photosensitive composition of the present invention contains a cationically polymerizable compound, the photosensitive composition and its cured product are suitable for the above-described uses.

BRIEF DESCRIPTION OF THE DRAWINGS

FIG. 1 is a view showing a graph obtained by measuring ultraviolet absorption before and after exposure of a coating film including Compound 1B that is the sulfonium salt of the present invention.

FIG. 2 is a view showing a graph obtained by measuring ultraviolet absorption before and after exposure of a coating film including Comparative Compound 1 that is the conventional sulfonium salt.

FIG. 3 is a view showing a graph obtained by performing measurement before and after exposure of a coating film including Compound 1B.

FIG. 4 is a view showing a graph obtained by performing $^1$H-NMR measurement before and after exposure of a coating film including Comparative Compound 1.

DESCRIPTION OF EMBODIMENTS

Sulfonium Salt

The sulfonium salt of the present invention is represented by the general formula (a1) and is that in a benzene ring in the general formula (a1), a methyl group is bonded to carbon atom present at an ortho position to carbon atom to which $A^1$ bonds. The sulfonium salt of the present invention has a methyl group at the above position, and therefore has high sensitivity to active energy rays as compared with the conventional sulfonium salt.

Sulfonium salt (z1) that is the conventional sulfonium salt is decomposed by irradiation with ultraviolet rays and generates highly reactive radical species. For example, it is considered that where highly reactive phenyl radicals are generated, a biphenyl compound having absorption in an ultraviolet region is by-produced. The biphenyl compound absorbs ultraviolet rays, and ultraviolet rays reaching the sulfonium salt (z1) are decreased. As a result, it is presumed that the sulfonium salt (z1) is difficult to enhance sensitivity to ultraviolet rays.

On the other hand, it is considered that the sulfonium salt of the present invention is decomposed by irradiation with ultraviolet rays to generate chemical species represented by the following formula (a7) and chemical species represented by the following formula (a8). In the chemical species represented by the formula (a8), methyl group is bonded to a benzene ring. Therefore, it is presumed that phenyl radicals having high reaction activity are difficult to be formed, thereby by-production of a biphenyl compound having absorption in an ultraviolet region is suppressed. As a result, ultraviolet rays reaching the sulfonium salt of the present invention are difficult to be decreased, and it is therefore presumed that the sulfonium salt of the present invention is easy to enhance sensitivity to ultraviolet rays as compared with the conventional sulfonium salt.

[Chemical formula 8]

(a7)

(a8)

In the general formula (a1), $R^1$ and $R^2$ each are preferably a group represented by the general formula (a2). $R^1$ and $R^2$ may be the same or different.

In the general formula (a1), when $R^1$ and $R^2$ are combined to form a ring together with the sulfur atom in the formula, the ring formed is preferably 3 to 10-membered rings including sulfur atom, and more preferably 5 to 7-membered rings. The ring formed may be a polycyclic ring and is preferably a ring formed by condensation of 5 to 7-membered rings.

In the general formula (a1), $R^3$ is preferably a group represented by the general formula (a3).

In the general formula (a1), $A^1$ is preferably S or O, and more preferably S.

In the general formula (a2), $R^4$ is preferably an alkyl group which may be substituted with a halogen atom, a hydroxy group, an alkylcarbonyl group, a thienylcarbonyl group, a furanylcarbonyl group, a selenophenylcarbonyl group, an amino group which may be substituted, or a nitro group, and more preferably an alkyl group which may be substituted with a halogen atom, an alkylcarbonyl group or a thienylcarbonyl group.

In the general formula (a2), m1 can be selected depending on the kind of a ring $Z^1$, and is, for example, an integer of 0 to 4, preferably an integer of 0 to 3, and more preferably an integer of 0 to 2.

In the general formula (a3), $R^5$ is preferably an alkylene group; an alkylene group substituted with a hydroxy group, an amino group which may be substituted, or a nitro group; or a group represented by the general formula (a5), and more preferably a group represented by the general formula (a5).

In the general formula (a3), $R^6$ is preferably an alkyl group; an alkyl group substituted with a hydroxy group, an amino group which may be substituted, or a nitro group; or a group represented by the general formula (a6), and more preferably a group represented by the general formula (a6).

In the general formula (a3), $A^2$ is preferably S or O, and more preferably S.

In the general formula (a3), n1 is preferably 0.

In the general formula (a4), $R^7$ and $R^8$ independently are preferably an alkylene group; an alkylene group substituted with a hydroxy group, an amino group which may be substituted, or a nitro group; or a group represented by the general formula (a5), and more preferably a group represented by the general formula (a5). $R^7$ and $R^8$ may be the same or different.

In the general formula (a4), $R^9$ and $R^{10}$ each are preferably a group represented by the general formula (a2). $R^9$ and $R^{10}$ may be the same or different.

In the general formula (a4), when $R^9$ and $R^{10}$ are combined to form a ring together with the sulfur atom in the formula, the ring formed is preferably 3 to 10-membered rings including sulfur atom in the formula, and more preferably 5 to 7-membered rings. The ring formed may be a polycyclic ring and is preferably a ring formed by condensation of 5 to 7-membered rings.

In the general formula (a4), $A^3$ is preferably S or O, and more preferably S.

In the general formula (a4), n2 is preferably 0.

In the general formula (a5), $R^{11}$ is preferably an alkyl group which may be substituted with a halogen atom, a hydroxy group, an amino group which may be substituted, or a nitro group, and more preferably an alkyl group which may be substituted with a halogen atom.

In the general formula (a5), m2 can be selected depending on the kind of a ring $Z^2$, and is, for example, an integer of 0 to 4, preferably an integer of 0 to 3, and more preferably an integer of 0 to 2.

In the general formula (a6), $R^{12}$ is preferably an alkyl group which may be substituted with a halogen atom, a hydroxy group, an alkylcarbonyl group, a thienylcarbonyl group, a furanylcarbonyl group, a selenophenylcarbonyl group, an amino group which may be substituted, or a nitro group, and more preferably an alkyl group which may be substituted with a halogen atom, an alkylcarbonyl group or a thienylcarbonyl group.

In the general formula (a6), m3 can be selected depending on the kind of a ring $Z^3$, and is, for example, an integer of 0 to 4, preferably an integer of 0 to 3, and more preferably an integer of 0 to 2.

In the general formula (a1), $X^-$ is a monovalent anion corresponding to an acid (HX) produced when the sulfonium salt of the present invention is irradiated with active energy rays (visible rays, ultraviolet rays, electron beams, X-rays and the like). When the sulfonium salt of the present invention is used as an acid generator, $X^-$ is preferably a monovalent polyatomic anion, and more preferably an anion represented by $MY_a^-$, $(Rf)_b PF_{6-b}^-$, $R^{x1}_c BY_{4-c}^-$, $R^{x1}_c GaY_{4-c}^-$, $R^{x2}SO_3^-$, $(R^{x2}SO_2)_3 C^-$ or $(R^{x2}SO_2)_2 N^-$. $X^-$ may be a halogen anion, and examples thereof include a fluoride ion, a chloride ion, a bromide ion and an iodide ion.

M represents phosphorus atom, boron atom or antimony atom.

Y represents a halogen atom (preferably fluorine atom).

Rf represents an alkyl group (preferably an alkyl group having 1 to 8 carbon atoms) in which 80 mol % or more of hydrogen atoms are substituted with fluorine atoms). Examples of the alkyl group as Rf by fluorine substitution include a linear alkyl group (such as methyl, ethyl, propyl, butyl, pentyl or octyl), a branched alkyl group (such as isopropyl, isobutyl, sec-butyl or tert-butyl) and a cycloalkyl group (such as cyclopropyl, cyclobutyl, cyclopentyl or cyclohexyl). The proportion that hydrogen atoms of the respective alkyl groups are substituted with fluorine atoms in Rf is preferably 80 mol % or more, more preferably 90% or more, and particularly preferably 100%, based on the mole number of hydrogen atoms in the original alkyl group. When the substitution proportion by fluorine atoms is within the preferred ranges, photosensitivity of the sulfonium salt is further satisfactory. Particularly preferred examples of Rf include $CF_3^-$, $CF_3CF_2^-$, $(CF_3)_2CF^-$, $CF_3CF_2CF_2^-$, $CF_3CF_2CF_2CF_2^-$, $(CF_3)_2CFCF_2^-$, $CF_3CF_2(CF_3)CF^-$ and $(CF_3)_3C^-$. $(Rf)_b$ each are independent, and therefore may be the same or different.

P represents phosphorus atom, and F represents fluorine atom.

$R^{x1}$ represents a phenyl group in which a part of hydrogen atoms is substituted with at least one element or electron withdrawing group. Example of the one element includes a halogen atom, and examples of the halogen atom include fluorine atom, chlorine atom and bromine atom. Examples of the electron withdrawing group include a trifluoromethyl group, a nitro group and a cyano group. Of those, a phenyl group in which one hydrogen atom is substituted with fluorine atom or a trifluoromethyl group is preferred. $R^{x1}_c$ each are independent, and therefore may be the same or different.

B represents boron atom, and Ga represents gallium atom.

$R^{x2}$ represents an alkyl group having 1 to 20 carbon atoms, a fluoroalkyl group having 1 to 20 carbon atoms or an aryl group having 6 to 20 carbon atoms, the alkyl group and fluoroalkyl group each may be a linear or branched group, and the alkyl group, fluoroalkyl group and aryl group each may be an unsubstituted group and may be a group having a substituent. Examples of the substituent include a hydroxy group, an amino group which may be substituted (for example, amino groups exemplified in the description hereinafter relating to the general formulae (a2) to (a6)), and a nitro group.

Carbon chain in the alkyl group, fluoroalkyl group or aryl group represented by $R^{x2}$ may have a hetero atom such as oxygen atom, nitrogen atom or sulfur atom. In particular, the carbon chain in the alkyl group or fluoroalkyl group represented by $R^{x2}$ may have a divalent functional group (such as an ether bond, a carbonyl bond, an ester bond, an amino bond, an amide bond, an imide bond, a sulfonyl bond, a sulfonylamide bond, a sulfonylimide bond or a urethane bond).

When the alkyl group, fluoroalkyl group or aryl group represented by $R^{x2}$ has the above-described substituent, hetero atom or functional group, the number of the substituent, hetero atom or functional group may be 1 and may be 2 or more.

S represents sulfur atom, O represents oxygen atom, C represents carbon atom, and N represents nitrogen atom.

a is an integer of 4 to 6.

b is preferably an integer of 1 to 5, more preferably an integer of 2 to 4, and particularly preferably 2 or 3.

c is preferably an integer of 1 to 4, and more preferably 4.

Example of the anion represented by $MY_a^-$ includes an anion represented by $SbF_6^-$, $PF_6^-$ or $BF_4^-$.

Preferred examples of the anion represented by $(Rf)_bPF_{6-b}^-$ include anions represented by $(CF_3CF_2)PF_4^-$, $(CF_3CF_2)_3PF_3^-$, $((CF_3)_2CF)_2PF_4^-$, $((CF_3)_2CF)_3PF_3^-$, $(CF_3CF_2CF_2)_2PF_4^-$, $(CF_3CF_2CF_2)_3PF_3^-$, $((CF_3)_2CFCF_2)_2PF_4^-$, $((CF_3)_2CFCF_2)_3PF_3^-$, $(CF_3CF_2CF_2CF_2)_2PF_4^-$ and $(CF_3CF_2CF_2CF_2)_3PF_3^-$. Of those, anions represented by $(CF_3CF_2)_3PF_3^-$, $(CF_3CF_2CF_2)_3PF_3^-$, $((CF_3)_2CF)_3PF_3^-$, $((CF_3)_2CF)_2PF_4^-$, $((CF_3)_2CFCF_2)_3PF_3^-$ and $((CF_3)_2CFCF_2)_2PF_4^-$ are preferred.

Examples of the anion represented by $R^{x1}_cBY_{4-c}^-$ include anions represented by $(C_6F_5)_4B^-$, $((CF_3)_2C_6H_3)_4B^-$, $(CF_3C_6H_4)_4B^-$, $(C_6F_5)_2BF_2^-$, $C_6F_5BF_3^-$ and $(C_6H_3F_2)_4B^-$. Of those, anions represented by $(C_6F_5)_4B^-$ and $((CF_3)_2C_6H_3)_4B^-$ are preferred.

Examples of the anion represented by $R^{x1}_cGaY_{4-c}^-$ include anions represented by $(C_6F_5)_4Ga^-$, $((CF_3)_2C_6H_3)_4Ga^-$, $(CF_3C_6H_4)_4Ga^-$, $(C_6F_5)_2GaF_2^-$, $C_6F_5GaF_3^-$ and $(C_6H_3F_2)_4Ga^-$. Of those, anions represented by $(C_6F_5)_4Ga^-$ and $((CF_3)_2C_6H_3)_4Ga$ are preferred.

Examples of the anion represented by $R^{x2}SO_3^-$ include trifluoromethanesulfonate anion, pentafluoroethanesulfonate anion, heptafluoropropanesulfonate anion, nonafluorobutanesulfonate anion, pentafluorophenylsulfonate anion, p-toluenesulfonate anion, benzenesulfonate anion, camphorsulfonate anion, methanesulfonate anion, ethanesulfonate anion, propanesulfonate anion and butanesulfonate anion. Of those, trifluoromethanesulfonate anion, nonafluorobutanesulfonate anion, methanesulfonate anion, butanesulfonate anion, camphorsulfonate anion, benzenesulfonate anion and p-toluenesulfonate anion are preferred.

Examples of the anion represented by $(R^{x2}SO_2)_3C^-$ include $(CF_3SO_2)_3C^-$, $(C_2F_5SO_2)_3C^-$, $(C_3F_7SO_2)_3C^-$ and $(C_4F_9SO_2)_3C^-$.

Examples of the anion represented by $(R^{x2}SO_2)_2N^-$ include $(CF_3SO_2)_2N^-$, $(C_2F_5SO_2)_2N^-$, $(C_3F_7SO_2)_2N^-$ and $(C_4F_9SO_2)_2N^-$.

Examples of the monovalent polyatomic anion that can be used include $MY_a^-$, $(Rf)_bPF_{6-b}^-$, $R^{x1}_cBY_{4-c}^-$, $R^{x1}_cGaY_{4-c}^-$, $R^{x2}SO_3^-$, $(R^{x2}SO_2)_3C^-$ and $(R^{x2}SO_2)_2N^-$, and further include a perhalogen acid ion (such as $ClO_4^-$ or $BrO_4^-$), a halogenated sulfonate ion (such as $FSO_3^-$ or $ClSO_3^-$), a sulfate ion (such as $CH_3SO_4^-$, $CF_3SO_4^-$ or $HSO_4^-$), a carbonate ion (such as $HCO_3^-$ or $CH_3CO_3^-$), an aluminate ion (such as $AlCl_4^-$ and $AlF_4^-$), a hexafluorobismuthate ion ($BiF_6^-$), a carboxylate ion (such as $CH_3COO^-$, $CF_3COO^-$, $C_6H_5COO^-$, $CH_3C_6H_4COO^-$, $C_6F_5COO^-$ or $CF_3C_6H_4COO^-$), an arylborate ion (such as $B(C_6H_5)_4^-$ or $CH_3CH_2CH_2CH_2B(C_6H_5)_3^-$), a thiocyanate ion ($SCN^-$) and a nitrate ion ($NO_3^-$).

Of those $X^-$, from standpoint of cationic polymerization performance, anions represented by $MY_a^-$, $(Rf)_bPF_{6-b}^-$, $R^{x1}_cBY_{4-c}^-$, $R^{x1}_cGaY_{4-c}^-$ and $(R^{x2}SO_2)_3C^-$ are preferred, and $SbF_6^-$, $PF_6^-$, $(CF_3CF_2)_3PF_3^-$, $(C_6F_5)_4B^-$, $—((CF_3)_2C_6H_3)_4B^-$, $(C_6F_5)_4Ga^-$, $((CF_3)_2C_6H_3)_4Ga^-$ and $(CF_3SO_2)_3C^-$ are particularly preferred.

Examples of the aromatic hydrocarbon ring in the general formulae (a2), (a5) and (a6) include a benzene ring and a condensed polycyclic aromatic hydrocarbon ring [for example, a condensed bicyclic hydrocarbon ring (for example, $C_{8-20}$ condensed bicyclic hydrocarbon ring such as a naphthalene ring, preferably $C_{10-16}$ condensed bicyclic hydrocarbon ring), and condensed bi- to tetracyclic aromatic hydrocarbon rings such as a condensed tricyclic aromatic hydrocarbon ring (for example, anthracene ring or a phenanthrene ring)]. The aromatic hydrocarbon ring is preferably a benzene ring or a naphthalene ring, and more preferably a benzene ring.

Examples of the halogen atom in the general formulae (a1) to (a6) include fluorine atom, chlorine atom, bromine atom and iodine atom.

Examples of the alkyl group in the general formulae (a1) to (a6) include a linear alkyl group having 1 to 18 carbon atoms (such as methyl, ethyl, n-propyl, n-butyl, n-pentyl, n-octyl, n-decyl, n-dodecyl, n-tetradecyl, n-hexadecyl or n-octadecyl), a branched alkyl group having 3 to 18 carbon atoms (such as isopropyl, isobutyl, sec-butyl, tert-butyl, isopentyl, neopentyl, tert-pentyl, isohexyl or isooctadecyl) and a cycloalkyl group having 3 to 18 carbon atoms (such as cyclopropyl, cyclobutyl, cyclopentyl, cyclohexyl or 4-decylcyclohexyl). Particularly, the alkyl group which may be substituted with a halogen atom in the general formulae (a1), (a2) and (a4) to (a6) means an alkyl group and an alkyl group substituted with a halogen atom. Examples of the alkyl group substituted with a halogen atom include groups in which at least one hydrogen atom in the linear alkyl group, branched alkyl group or cycloalkyl group has been substituted with a halogen atom (such as monofluoromethyl, difluoromethyl or trifluoromethyl). Of the alkyl groups which may be substituted with a halogen atom, $R^1$, $R^2$, $R^9$ and $R^{10}$ each are particularly preferably trifluromethyl group, and $R^4$, $R^6$, $R^{11}$ and $R^{12}$ each are particularly preferably methyl group.

Examples of the alkoxy group in the general formulae (a2) to (a6) include linear or branched alkoxy groups having 1 to 18 carbon atoms (such as methoxy, ethoxy, propoxy, isopropoxy, butoxy, isobutoxy, sec-butoxy, tert-butoxy, hexyloxy, decyloxy, dodecyloxy and octadecyloxy).

Examples of the alkyl group in the alkylcarbonyl group in the general formulae (a2) to (a6) include the above-described linear alkyl group having 1 to 18 carbon atoms, branched alkyl group having 3 to 18 carbon atoms and cycloalkyl group having 3 to 18 carbon atoms. Examples of the alkylcarbonyl group include a linear, branched or cyclic alkylcarbonyl groups having 2 to 18 carbon atoms (such as acetyl, propionyl, butanoyl, 2-methylpropionyl, heptanoyl, 2-methylbutanoyl, 3-methylbutanoyl, octanoyl, decanoyl, dodecanoyl, octadecanoyl, cyclopentanoyl and cyclohexanoyl).

Examples of the arylcarbonyl group in the general formulae (a3) to (a6) include arylcarbonyl groups having 7 to 11 carbon atoms (such as benzoyl and naphthoyl).

Examples of the alkoxycarbonyl group in the general formulae (a2) to (a6) includes linear or branched alkoxycarbonyl groups having 2 to 19 carbon atoms (such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, octyloxycarbonyl, tetradecyloxycarbonyl and octadecyloxycarbonyl).

Examples of the aryloxycarbonyl group in the general formulae (a3) to (a6) include aryloxycarbonyl groups having 7 to 11 carbon atoms (such as phenoxycarbonyl and naphthoxycarbonyl).

Examples of the arylthiocarbonyl group in the general formulae (a3) to (a6) includes arylthiocarbonyl groups having 7 to 11 carbon atoms (such as phenylthiocarbonyl and naphthoxythiocarbonyl).

Examples of the acyloxy group in the general formulae (a2) to (a6) include linear or branched acyloxy groups having 2 to 19 carbon atoms (such as acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, tetradecylcarbonyloxy and octadecylcarbonyloxy).

Examples of the arylthio group in the general formulae (a3) to (a6) include arylthio groups having 6 to 20 carbon atoms (such as phenylthio, 2-methylphenylthio, 3-methylphenylthio, 4-methylphenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio)benzoyl]phenylthio, 4-[4-(phenylthio)phenoxy]phenylthio, 4-[4-(phenylthio)phenyl]phenylthio, 4-(phenylthio)phenylthio, 4-benzoylphenylthio, 4-benzoyl-2-chlorophenylthio, 4-benzoyl-3-chlorophenylthio, 4-benzoyl-3-methylthiophenylthio, 4-benzoyl-2-methylthiophenylthio, 4-(4-methylthiobenzoyl)phenylthio, 4-(2-methylthiobenzoyl)phenylthio, 4-(p-methylbenzoyl)phenylthio, 4-(p-ethylbenzoyl)phenylthio, 4-(p-isopropylbenzoyl) phenylthio and 4-(p-tert-butylbenzoyl)phenylthio).

Examples of the alkylthio group in the general formulae (a2) to (a6) include linear or branched alkylthio groups having 1 to 18 carbon atoms (such as methylthio, ethylthio, propylthio, isopropylthio, butylthio, isobutylthio, sec-butylthio, tert-butylthio, pentylthio, isopentylthio, neopentylthio, tert-pentylthio, octylthio, decylthio, dodecylthio and isooctadecylthio).

Examples of the aryl group in the general formulae (a3) to (a6) include aryl groups having 6 to 10 carbon atoms (such as phenyl, tolyl, dimethylphenyl and naphthyl).

Examples of the heterocyclic aliphatic hydrocarbon group in the general formula (a2) include heterocyclic aliphatic hydrocarbon groups having 2 to 20 (preferably 4 to 20) carbon atoms (such as pyrrolidinyl, tetrahydrofuranyl, tetrahydrothienyl, pipepiridinyl, tetrahydropyranyl, tetrahydrothiopyranyl and morphorinyl).

Examples of the heterocyclic hydrocarbon group in the general formulae (a3) to (a6) include heterocyclic hydrocarbon groups having 4 to 20 carbon atoms (such as thienyl, furanyl, selenophenyl, pyranyl, pyrrolyl, oxazolyl, thiazolyl, pyrridyl, pyrimidyl, pyradinyl, indolyl, benzofuranyl, benzothienyl, quinolyl, isoquinolyl, quinoxalinyl, quinazolinyl, carbazolyl, acridinyl, phenothiadinyl, phenadinyl, xanthenyl, thianthrenyl, phenoxadinyl, phenoxathiinyl, chromanyl, isochromanyl, dibenzothienyl, xanthonyl, thioxanthonyl and dibenzofuranyl).

Examples of the aryloxy group in the general formulae (a3) to (a6) include aryloxy groups having 6 to 10 carbon atoms (such as phenoxy and naphthyloxy).

Examples of the alkylsulfinyl group in the general formulae (a2) to (a6) include linear or branched sulfinyl groups having 1 to 18 carbon atoms (such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, tert-pentylsulfinyl, octylsufinyl and isooctadecylsulfinyl).

Examples of the arylsulfinyl group in the general formulae (a3) to (a6) include arylsulfinyl groups having 6 to 10 carbon atoms (such as phenylsulfinyl, tolylsulfinyl and naphthylsulfinyl).

Examples of the alkylsulfonyl group in the general formulae (a2) to (a6) include linear or branched alkylsulfonyl groups having 1 to 18 carbon atoms (such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, octylsufonyl and octadecylsulfonyl).

Examples of the arylsulfonyl group in the general formulae (a3) to (a6) include arylsulfonyl groups having 6 to 10 carbon atoms (such as phenylsulfonyl, tolylsulfonyl (tosyl) and naphthylsulfonyl).

Examples of the hydroxy(poly)alkyleneoxy group in the general formulae (a2) to (a6) include hydroxy(poly)alkyleneoxy groups represented by $HO(AO)_q$— (wherein AO independently represents an ethyleneoxy group and/or a propyleneoxy group, and q is an integer of 1 to 5).

Examples of the amino group which may be substituted in the general formulae (a2) to (a6) include an amino group ($-NH_2$) and substituted amino groups having 1 to 15 carbon atoms (such as methylamino, dimethylamino, ethylamino, methylethylamino, diethylamino, n-propylamino, methyl-n-propylamino, ethyl-n-propylamino, n-propylamino, isopropylamino, isopropylmethylamino, isopropylethylamino, diisopropylamino, phenylamino, diphenylamino, methylphenylamino, ethylphenylamino, n-propylphenylamino and isopropylphenylamino).

Examples of the alkylene group in the general formulae (a3) and (a4) include linear or branched alkylene groups having 1 to 18 carbon atoms (such as methylene, 1,2-ethylene, 1,1-ethylene, propane-1,3-diyl, propane-1,2-diyl, propane-1,1-diyl, propane-2,2-diyl, butane-1,4-diyl, butane-1,3-diyl, butane-1,2-diyl, butane-1,1-diyl, butane-2,2-diyl, butane-2,3-diyl, pentane-1,5-diyl, pentane-1,4-diyl, hexane-1,6-diyl, heptane-1,7-diyl, octane-1,8-diyl, 2-ethylhexane-1,6-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl and hexadecane-1,16-diyl).

The sulfonium salt of the present invention can be synthesized, for example, according to the following scheme. Specifically, a compound represented by the following general formula (b2) is reacted with 1-fluoro-2-methyl-4-nitrobenzene represented by the following formula (b1) in the presence of a base such as potassium hydroxide to obtain a nitro compound represented by the following general formula (b3). The nitro compound is reduced in the presence of reduced iron to obtain an amine compound represented by the following general formula (b4). The amine compound is reacted with a nitrite (for example, sodium nitrile) represented by $MaNO_2$ (wherein Ma represents a metallic atom, for example, an alkali metal atom such as a sodium atom) to obtain a diazo compound. The diazo compound is mixed with cuprous halide represented by CuX' (wherein X' represents a halogen atom such as bromine atom; hereinafter the same) and hydrogen halide represented by HX'. The reaction of the resulting mixture is conducted to obtain a halide represented by the following general formula (b5). Grignard reagent is prepared from the halide and magnesium. The Grignard reagent is reacted with a sulfoxide compound represented by the following general formula (b6) in the presence of chlorotrimethylsilane. Thus, a sulfonium salt represented by the following general formula (b7) can be obtained. The sulfonium salt is further reacted with a salt represented by $Mb^+X''^-$ (wherein $Mb^+$ represents a metallic cation, for example, an alkali metal cation such as potassium ion, and X" represents a monovalent anion represented by $X^-$ (excluding a halogen anion)), followed by conducting salt exchange. Thus, a sulfonium salt represented by the following general formula (b8) can be obtained. $R^1$ to $R^3$ and $A^1$ in the general formulae (b2) to (b8) are the same as defined in the general formula (1).

Scheme

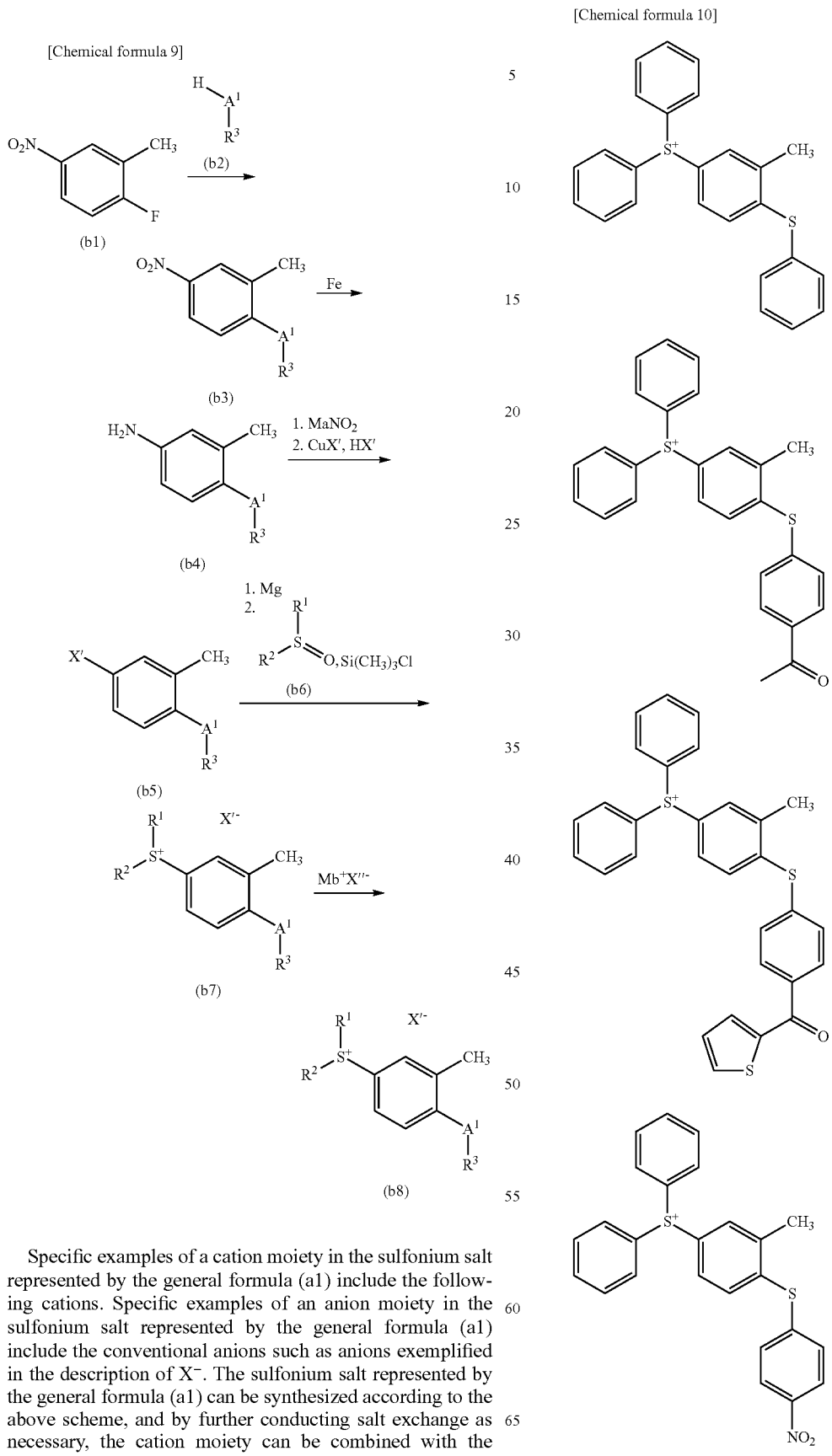

Specific examples of a cation moiety in the sulfonium salt represented by the general formula (a1) include the following cations. Specific examples of an anion moiety in the sulfonium salt represented by the general formula (a1) include the conventional anions such as anions exemplified in the description of X$^-$. The sulfonium salt represented by the general formula (a1) can be synthesized according to the above scheme, and by further conducting salt exchange as necessary, the cation moiety can be combined with the desired anion moiety.

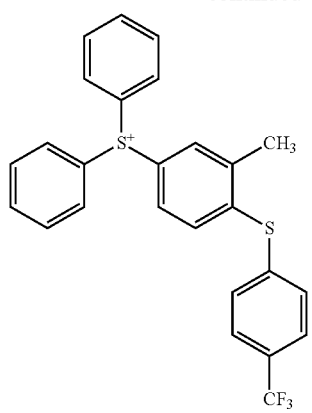
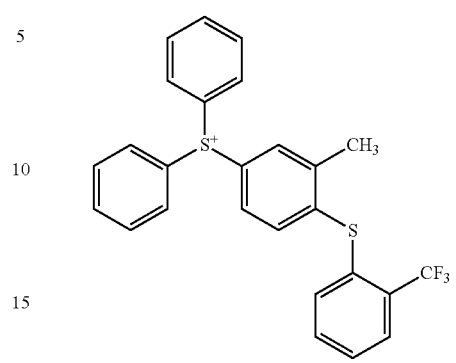
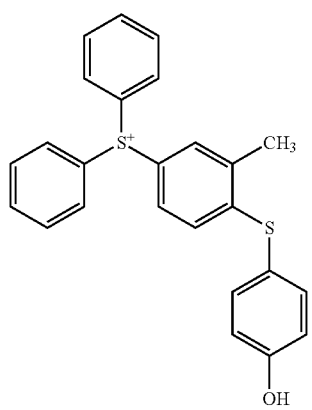
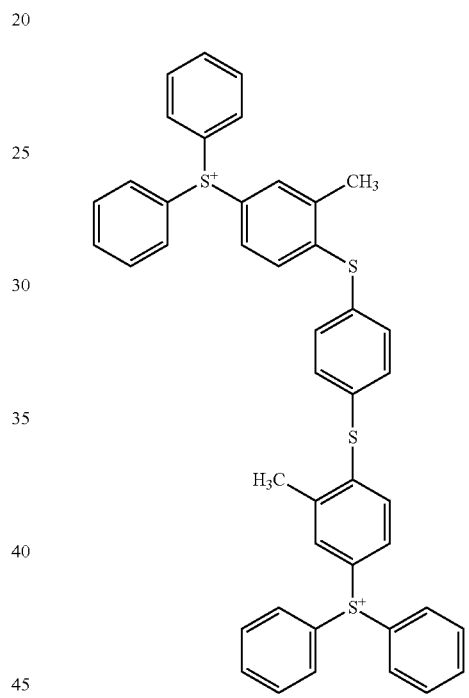
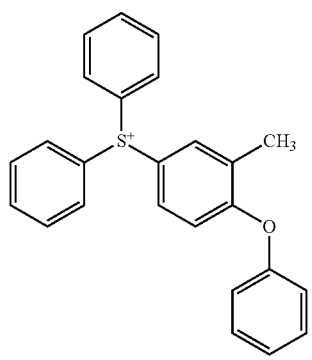
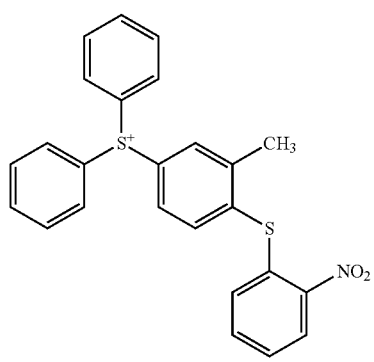
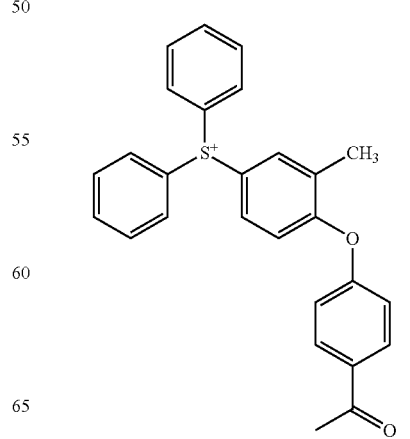

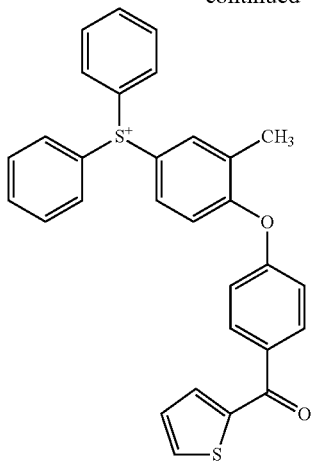

Photoacid Generator

The sulfonium salt of the present invention is preferably used as a photoacid generator.

The photoacid generator means a compound capable of producing an acid by decomposition of its chemical structure when irradiated with light. The acid produced can be used as a catalyst in, for example, a curing reaction of an epoxide. The photoacid generator of the present invention may be used alone and may be used together with other photoacid generator.

When other photoacid generator is used, the amount of the other photoacid generator used is preferably 1 to 100, and more preferably 5 to 50, per total mole number of the sulfonium salt of the present invention.

Examples of the other photoacid generator include the conventional photoacid generators such as a salt between an onium ion (such as sulfonium, iodonium, selenium, ammonium or phosphonium) or a transition metal complex ion and an anion.

The photoacid generator of the present invention may be previously dissolved in a solvent that does not inhibit a cationic polymerization in order to facilitate dissolution in a cationically polymerizable compound.

Examples of the solvent include a carbonate (such as propylene carbonate, ethylene carbonate, 1,2-butylene carbonate, dimethyl carbonate or diethyl carbonate); an ester (such as ethyl acetate, ethyl lactate, β-propiolactone, β-butyrolactone, γ-butyrolactone, δ-valerolactone or ε-caprolactone); an ether (such as ethylene glycol monomethyl ether, propylene glycol monoethyl ether, diethylene glycol monobutyl ether, dipropylene glycol dimethyl ether, triethylene glycol diethyl ether or tripropylene glycol dibutyl ether); and an ether ester (such as ethylene glycol monomethyl ether acetate, propylene glycol monoethyl ether acetate or diethylene glycol monobutyl ether acetate).

When the solvent is used, the proportion of the solvent used is preferably 15 to 1,000 parts by mass, and more preferably 30 to 500 parts by mass, per 100 parts by mass of the photoacid generator of the present invention.

Photosensitive Composition

The photosensitive composition of the present invention contains a photoacid generator including the sulfonium salt of the present invention, and includes, for example, a composition containing a photoacid generator including the sulfonium salt of the present invention, and a cationically polymerizable compound. In the photosensitive composition of the present invention, the photoacid generator may be used in one kind alone, and may be used as a mixture of two or more kinds thereof. Furthermore, the cationically polymerizable compound may be used in one kind alone and may be used as a mixture of two or more kinds thereof.

Examples of the cationically polymerizable compound include a cyclic ether (such as epoxide or oxetane), an ethylenically unsaturated compound (such as vinyl ether or styrene), bicycloorthoester, spiroorthocarbonate and spiroorthoester (Japanese Unexamined Patent Application, Publication Nos. H11-060996, H09-302269, 2003-026993, 2002-206017, H11-349895, H10-212343, 2000-119306, H10-67812, 2000-186071, H08-85775, H08-134405, 2008-20838, 2008-20839, 2008-20841, 2008-26660, 2008-26644, and 2007-277327, The Technical Association of Photopolymers, Japan "PHOTOPOLYMER HANDBOOK" (1989, Kogyo Chosakai Publishing Co., Ltd.), General Technical Center "Technology of UV.EB Curing" (1982, General Technical Center), Rad Tech Japan "UV.EB Curing Material" (1992, CMC), Technical Information Institute Co., Ltd. "Insufficient Curing.Inhibition Factor in UV Curing and Its Countermeasure" (2003, Technical Information Institute Co., Ltd.), COLORING MATERIAL, 68 (5), 286-293 (1995), FINE CHEMICAL, 29, (19), 5-14 (2000), and the like).

The epoxide can use the conventional epoxides, and examples thereof include an aromatic epoxide, an aplicyclic epoxide and an aliphatic epoxide.

Examples of the aromatic epoxide include glycidyl ether of a monohydric or polyhydric phenol having at least one aromatic ring (phenol, biphenol, bisphenol A, bisphenol F, phenol novolak, cresol novolak and their bromides or alkylene oxide adducts of those), and glycidyl ester (such as diglycidyl phthalate or diglycidyl 3-methylphthalate) of a monohydric or polyhydric carboxylic acid having at least one aromatic ring (such as phthalic acid or 3-methylphthalic acid).

Examples of the alicyclic epoxide include compounds obtained by epoxidizing a compound having at least one cyclohexene or cyclopentene ring with an oxidizing agent (such as 3,4-epoxycyclohexylmethyl-3,4-epoxycyclohexane carboxylate, 3,4-epoxy-1-methylcyclohexyl-3,4-epoxy-1-methylhexane carboxylate, 6-methyl-3,4-epoxycylcohexyl-methyl-3,4-epoxycyclo hexane carboxylate, 3,4-epoxy-3-methylcyclohexylmethyl-3,4-epoxy-3-methylcyclo hexane carboxylate, 3,4-epoxy-5-methylcyclohexylmethyl-3,4-epoxy-5-methylcyclo hexane carboxylate, 2-(3,4-epoxycyclohexyl-5,5-spiro-3,4-epoxy) cyclohexane metadioxane, bis(3,4-epoxycyclohexylmethyl) adipate, 3,4-epoxy-6-methylcyclohexyl carboxylate, methylenebis(3,4-epoxycyclohexane), dicyclopentadiene diepoxide and ethylenebis(3,4-epoxycyclohexane carboxylate).

Examples of the aliphatic epoxide include polyglycidyl ether of aliphatic polyhydric alcohol or alkylene oxide adduct thereof (such as 1,4-butanediol diglycidyl ether, 1,6-hexanediol diglycidyl ether, hydrogenated bisphenol A diglycidyl ether, triglycidyl ether of glycerin, triglycidyl ether of trimethylolpropane, tetraglycidyl ether of sorbitol or hexaglycidyl ether of dipentaerythritol), polyglycidyl ester of aliphatic polybasic acid (such as diglycidyl tetrahydrophthalate, diglycidyl hexahydrophthalate or diglycidyl-hexahydro-3-methyl phthalate), epoxide of long-chain unsaturated compound (such as epoxidized soybean oil or epoxidized polybutadiene), glycidyl-containing polymer (such as homopolymer of glycidyl (meth)acrylate or a copolymer of glycidyl (meth) acrylate and other unsaturated monomer), and polyfunctional epoxide having a dimethylsiloxane skeleton (Journal of Polym. Sci. Part A, Polym. Chem., Vol. 28, 497 (1990)).

The oxetane can use the conventional oxetanes, and examples thereof include 3-ethyl-3-hydroxymethyloxetane, (3-ethyl-3-oxetanylmethoxy)methylbenzene, [1-(3-ethyl-oxetanylmethoxy)ethyl]phenyl ether, isobutoxymethyl(3-ethyl-3-oxetanylmethyl)ether, isobornyloxyethyl(3-ethyl-3-oxetanylmethyl)ether, isobornyl(3-ethyl-3-oxetanylmethyl) ether, 2-ethylhexyl(3-ethyl-3-oxetanylmethyl)ether, ethyl diethylene glycol(3-ethyl-3-oxetanylmethyl)ether, dicyclopentenyloxyethyl(3-ethyl-3-oxetanylmethyl)ether, dicyclopentenyl(3-ethyl-3-oxetanylmethyl)ether, tetrahydrofurfuryl (3-ethyl-3-oxetanylmethyl)ether, tetrabromophenyl(3-ethyl-3-oxetanylmethyl)ether, 2-tetrabromophenoxyethyl(3-ethyl-3-oxetanylmethyl)ether, tribromophenyl(3-ethyl-3-oxetanylmethyl)ether, 2-tribromophenoxyethyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, butoxyethyl(3-ethyl-3-oxetanylmethyl)ether, pentachlorophenyl(3-ethyl-3-oxetanylmethyl)ether, pentabromophenyl(3-ethyl-3-oxetanylmethyl)ether, bornyl(3-ethyl-3-oxetanylmethyl) ether, 3,7-bis(3-oxetanyl)-5-oxanonane, 3,3'-(1,3-(2-methylenyl)propanediylbis(oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycolbis(3-ethyl-3-oxetanylmethyl)ether, dicyclopentenylbis(3-ethyl-3-oxetanylmethyl)ether, triethylene glycolbis(3-ethyl-3-oxetanylmethyl)ether, tetraethylene glycolbis (3-ethyl-oxetanylmethyl)ether, tricyclodecanediyldimethylene(3-ethyl-3-oxetanylmethyl)ether, trimethylolpropanetris(3-ethyl-3-oxetanylmethyl)ether, 1,4-bis(3-ethyl-3-oxetanylmethoxy)butane, 1,6-bis(3-ethyl-3-oxetanylmethoxy)hexane, pentaerythritoltris(3-ethyl-3-oxetanylmethyl)ether, pentaerythritoltetrakis(3-ethyl-3-oxetanylmethyl)ether, polyethylene glycolbis(3-ethyl-3-oxetanylmethyl)ether, dipentaerythritolhexakis(3-ethyl-3-oxetanylmethyl)ether, dipentaerythritolpentakis(3-ethyl-3-oxetanylmethyl)ether, dipentaerythritoltetrakis(3-ethyl-3-oxetanylmethyl)ether, 3-ethyl-3-phenoxymethyloxetane, 3-ethyl-3-(4-methylphenoxy)methyloxetane, 3-ethyl-3-(4-fluorophenoxy)methyloxetane, 3-ethyl-3-(1-naphthoxy) methyloxetane, 3-ethyl-3-(2-naphthoxy)methyloxetane, 3-ethyl-3-{[3-(ethoxysilyl)propoxy]methyl}oxetane, oxetanylsilsesquioxetane and phenol novolak oxetane.

The ethylenically unsaturated compound can use the conventional cationically polymerizable monomers, and examples thereof include aliphatic monovinyl ether, aromatic monovinyl ether, polyfunctional vinyl ether, styrene and cationically polymerizable nitrogen-containing monomer.

Examples of the aliphatic monovinyl ether include methyl vinyl ether, ethyl vinyl ether, butyl vinyl ether, isobutyl vinyl ether, cyclohexyl vinyl ether, 2-chloroethyl vinyl ether, 2-hydroxyethyl vinyl ether, 4-hydroxybutyl vinyl ether, stearyl vinyl ether, 2-acetoxyethyl vinyl ether, diethylene glycol monovinyl ether, 2-ethylhexyl vinyl ether, dodecyl vinyl ether, octadecyl vinyl ether, allyl vinyl ether, 2-methacryloyloxyethyl vinyl ether and 2-acryloyloxyethyl vinyl ether.

Examples of the aromatic monovinyl ether include 2-phenoxyethyl vinyl ether, phenyl vinyl ether and p-methoxyphenyl vinyl ether.

Examples of the polyfunctional vinyl ether include butanediol-1,4-divinyl ether, triethylene glycol divinyl ether, 1,4-benzene divinyl ether, hydroquinone divinyl ether, cyclohexane dimethanol divinyl ether (1,4-bis[(vinyloxy)methyl]cyclohexane), diethylene glycol divinyl ether, dipropylene glycol divinyl ether and hexanediol divinyl ether.

Examples of the styrene include styrene, α-methylstyrene, p-methoxystyrene and p-tert-butoxystyrene.

Examples of the cationically polymerizable nitrogen-containing monomer includes N-vinylcarbazol and N-vinylpyrrolidone.

Examples of the bicycloorthoester include 1-phenyl-4-ethyl-2,6,7-trioxabicyclo[2.2.2]octane and 1-ethyl-4-hydroxymethyl-2,6,7-trioxabicyclo-[2.2.2]octane.

Examples of the spiro orthocarbonate include 1,5,7,11-tetraoxaspiro[5.5]undecane and 3,9-dibenzyl-1,5,7,11-tetraoxaspiro[5.5]undecane.

Examples of the spiro ortho ester include 1,4,6-trioxaspiro[4.4]nonane, 2-methyl-1,4,6-trioxaspiro[4.4]nonane and 1,4,6-trioxaspiro[4.5]decane.

Of those cationically polymerizable compounds, epoxide, oxetane and vinyl ether are preferred, epoxide and oxetane is more preferred, and alicyclic epoxide and oxetane are particularly preferred. Those cationically polymerizable compounds may be used alone or as mixtures of two or more thereof.

The content of the photoacid generator of the present invention in the photosensitive composition is preferably 0.05 to 20 parts by mass, and more preferably 0.1 to 10 parts by mass, per 100 parts by mass of the cationically polymerizable compound. When the content is within this range, polymerization of the cationically polymerizable compound is further enhanced, and properties of a cured product are further satisfactory. The content of the photoacid generator is determined considering various factors such as properties of the cationically polymerizable compound, kind and irradiation amount of energy rays, temperature, curing time, humidity, thickness of coating film, and the like, and is not limited to the above range.

As necessary, the photosensitive composition of the present invention can contain the conventional additives (such as a sensitizer, a pigment, a filler, an antistatic agent, a flame retardant, a defoaming agent, a fluidity control agent, a light stabilizer, an antioxidant, an adhesion-imparting agent, an ion scavenger, a coloration inhibitor, a solvent, a non-reactive resin and a radically polymerizable compound).

The photosensitive composition of the present invention does not basically require a sensitizer, but as necessary, can contain the sensitizer as a material to assist curing. Examples of the sensitizer can use the conventional sensitizers (for example, Japanese Unexamined Patent Application, Publication Nos. H11-279212 and H09-183960, and examples thereof include anthracene {such as anthracene, 9,10-dibutoxyanthracene, 9,10-dimethoxyanthracene, 2-ethyl-9,10-dimethoxyanthracene, 2-tert-butyl-9,10-dimethoxyanthracene, 2,3-dimethyl-9,10-dimethoxyanthracene, 9-methoxy-10-methylanthracene, 9,10-diethoxyanthracene, 2-ethyl-9,10-diethoxyanthracene, 2-tert-butyl-9,10-diethoxyanthracene, 2,3-dimethyl-9,10-diethoxyanthracene, 9-ethoxy-10-methylanthracene, 9,10-dipropoxyanthracene, 9,10-diisopropoxyanthracene, 9,10-diethoxyanthracene, 2-ethyl-9,10-dipropoxyanthracene, 2-tert-butyl-9,10-dipropoxyanthracene, 2,3-dimethyl-9,10-dipropoxyanthracene, 9-isopropoxy-10-methylanthracene, 9,10-dibenzyloxyanthracene, 2-ethyl-9,10-dibenzyloxyanthracene, 2-tert-9,10-dibenzyloxyanthracene, 2,3-dimethyl-9,10-dibenzyloxyanthracene, 9-benzyloxy-10-methylanthracene, 9,10-di-α-methylbenzyloxyanthracene, 2-ethyl-9,10-di-α-methylbenzyloxyanthracene, 2-tert-9,10-di-α-methylbenzyloxyanthracene, 2,3-dimethyl-9,10-di-α-methylbenzyloxyanthracene, 9-(α-methylbenzyloxy)-10-methylanthracene, 9,10-diphenylanthracene, 9-methoxyanthracene, 9-ethoxyanthracene, 9-methylanthracene, 9-bromoanthracene, 9-methylthioanthracene or 9-ethylthioanthracene}; pyrene; 1,2-benzanthracene; perylene; tetracene; coronene; thioxanthone {such as thioxanthone, 2-methylthioxanthone, 2-ethylthioxanthone, 2-chlorothioxanthone, 2-isopropylthioxanthone or 2,4-diethylthioxanthone}; phenothiazine and its derivative {such as phenothiazine, N-methylphenothiazine, —N-ethylphenothiazine or N-phenylphenothiazine}; xanthone; naphthalene {such as 1-naphthol, 2-naphthol, 1-methoxynaphthalene, 2-methoxynaphthalene, 1,4-dihydroxynaphthalene, 1,5-dihydroxynaphthalene, 1,6-dihydroxynaphthalene, 2,7-dihydroxynaphthalene, 2,7-dimethoxynaphthalene, 1,1'-thiobis(2-naphthol), 1,1'-bi-(2-naphthol) or 4-methoxy-1-naphthaol}; ketone {such as dimethoxyacetophenone, diethoxyacetophenone, 2-hydroxy-2-methyl-1-phenylpropan-1-one, 4'-isopropyl-2-hydroxy-2-methylpropiophenone, 2-hydroxymethyl-2-methylpropiophenone, 2,2-dimethoxy-1,2-diphenylethan-1-one, p-dimethylaminoacetophenone, p-tert-butyldichloroacetophenone, p-tert-butyltrichloroacetophenone, p-azidobenzalacetophenone, 1-hydroxycyclohexyl phenyl ketone, benzoin, benzoin methyl ether, benzoin ethyl ether, benzoin isopropyl ether, benzoin-n-butyl ether, benzoin isobutyl ether, 1-[4-(2-hydroxyethoxy)phenyl]-2-hydroxy-2-methyl-1-propan-1-one, benzophenone, methyl o-benzoyl benzoate, Michler ketone, 4,4'-bisdiethylaminobenzophenone, 4,4'-dichlorobenzophenone or 4-benzoyl-4'-methyldiphenyl sulfide}; carbazole {such as N-phenylcarbazole, N-ethylcarbazole, poly-N-vinylcarbazole or N-glycidyl carbazole}; chrysene {such as 1,4-dimethoxychrysene, 1,4-diethoxychrysene, 1,4-dipropoxychrysene, 1,4-dibenzyloxychrysene or 1,4-di-α-methylbenzyloxychrysene}; and phenanthrene {such as 9-hydroxyphenanthrene, 9-methoxyphenanthrene, 9-ethoxyphenanthrene, 9-benzyloxyphenanthrene, 9,10-dimethoxyphenanthrene, 9,10-diethoxyphenanthrene, 9,10-dipropoxyphenanthrene, 9,10-dibenzyloxyphenanthrene, 9,10-di-α-methylbenzyloxyphenanthrene, 9-hydroxy-10-methoxyphenanthrene or 9-hydroxy-10-ethoxyphenanthrene}.

When the photosensitive composition contains the sensitizer, the content of the sensitizer is preferably 1 to 300 parts by mass, and more preferably 5 to 200 parts by mass, per 100 parts by mass of the photoacid generator.

The pigment can use the conventional pigments, and examples thereof include an inorganic pigment (such as titanium oxide, iron oxide or carbon black) and an organic pigment (such as azo pigment, cyanine pigment, phthalocyanine pigment or quinacridone pigment).

When the photosensitive composition contains the pigment, the content of the pigment is preferably 0.5 to 400,000 parts by mass, and more preferably 10 to 150,000 parts by mass, per 100 parts by mass of the photoacid generator.

The filler can use the conventional fillers, and examples thereof include fused silica, crystalline silica, calcium carbonate, aluminum oxide, aluminum hydroxide, zirconium oxide, magnesium carbonate, mica, talc, calcium silicate and aluminum lithium silicate.

When the photosensitive composition contains the filler, the content of the filler is preferably 50 to 600,000 parts by mass, and more preferably 300 to 200,000 parts by mass, per 100 parts by mass of the photoacid generator.

The antistatic agent can use the conventional antistatic agents, and examples thereof include a non-ionic antistatic agent {such as glycerin fatty acid ester, polyoxyethylene alkyl ether, polyoxyethylene alkyl phenol ether, N,N-bis(2-hydroxyethyl)alkylamine, polyoxyethylene alkylamine, polyoxyethylene alkylamine fatty acid ester or alkyl diethanolamine}; an anionic antistatic agent {such as alkyl sulfonate, alkylbenzene sulfonate or alkyl phosphate}; a cationic antistatic agent {such as tetraalkyl ammonium salt or trialkylbenzyl ammonium salt}; an amphoteric antistatic agent {such as alkyl betaine or alkylimidazoliumbetaine}; and a polymeric antistatic agent {such as quaternary ammonio-containing styrene-(meth)acrylate copolymer, quaternary ammonio-containing styrene-acrylonitrile-maleimide copolymer, polyoxyethylene glycol, polyether ester amide, polyether amide imide, ethylene oxide-epichlorohydrin copolymer or methoxypolyoxyethylene glycol (meth)acrylate copolymer}.

When the photosensitive composition contains the antistatic agent, the content of the antistatic agent is preferably 0.1 to 20,000 parts by mass, and more preferably 0.6 to 5,000 parts by mass, per 100 parts by mass of the photoacid generator.

The flame retardant can use the conventional flame retardants, and examples thereof include an inorganic flame retardant {such as antimony trioxide, antimony pentoxide, tin oxide, tin hydroxide, molybdenum oxide, zinc borate, barium metaborate, red phosphorus, aluminum hydroxide, magnesium hydroxide or calcium aluminate}; a bromine flame retardant {such as tetrabromophthalic anhydride, hexabromobenzene or decabromobiphenyl ether}; and a phosphate flame retardant {such as tris(tribromophenyl) phosphate}.

When the photosensitive composition contains the flame retardant, the content of the flame retardant is preferably 0.5 to 40,000 parts by mass, and more preferably 5 to 10,000 parts by mass, per 100 parts b mass of the photoacid generator.

The defoaming agent can use the conventional defoaming agents, and examples thereof include an alcohol defoaming agent {such as isopropanol, n-butanol, octaethyl alcohol or hexadecyl alcohol}; a metal soap defoaming agent {such as calcium stearate or aluminum stearate}; a phosphoric ester defoaming agent {such as tributyl phosphate}; a fatty acid ester defoaming agent {such as glycerin monolaurate}; a polyether defoaming agent {such as polyalkylene glycol}; a silicone defoaming agent {such as dimethyl silicone oil or silica.silicone compound}; and a mineral oil defoaming agent {such as a mineral oil having a silica powder dispersed therein}.

When the photosensitive composition contains the defoaming agent, the content of the defoaming agent is preferably 0.1 to 20,000 parts by mass, and more preferably 0.5 to 5,000 parts by mass, per 100 parts by mass of the photoacid generator.

The fluidity control agent can use the conventional fluidity control agents, and examples thereof include hydrogenated castor oil, polyethylene oxide, organic bentonite, colloidal silica, amide wax, metal soap and acrylic ester polymer.

When the photosensitive composition contains the fluidity control agent, the content of the fluidity control agent is preferably 0.1 to 20,000 parts by mass, and more preferably 0.5 to 5,000 parts by mass, per 100 parts by mass of the photoacid generator.

The light stabilizer can use the conventional light stabilizers, and examples thereof include an ultraviolet absorption stabilizer {such as benzotriazole, benzophenone, salycylate, cyanoacrylate or their derivatives}; a radicalscavenging type stabilizer {such as hindered amine}; and a quenching type stabilizer {such as nickel complex}.

When the photosensitive composition contains the light stabilizer, the content of the light stabilizer is preferably 0.05 to 40,000 parts by mass, and more preferably 0.5 to 10,000 parts by mass, per 100 parts by mass of the photoacid generator.

The antioxidant can use the conventional antioxidants, and examples thereof include a phenol-based antioxidant {such as monophenol-based, bisphenol-based or polyphenol-based}, a sulfur-based antioxidant and a phosphorus-based antioxidant.

When the photosensitive composition contains the antioxidant, the content of the antioxidant is preferably 0.1 to 20,000 parts by mass, and more preferably 0.6 to 5,000 parts by mass, per 100 parts by mass of the photoacid generator.

The adhesion-imparting agent can use the conventional adhesion-imparting agents, and examples thereof include a coupling agent, a silane coupling agent and a titanium coupling agent.

When the photosensitive composition contains the adhesion-imparting agent, the content of the adhesion-imparting agent is preferably 0.1 to 20,000 parts by mass, and more preferably 0.6 to 5,000 parts by mass, per 100 parts by mass of the adhesion-imparting agent.

The ion scavenger can use the conventional ion scavengers, and example thereof includes organic aluminum {such as alkoxyaluminum or phenoxyaluminum}.

When the photosensitive composition contains the ion scavenger, the content of the ion scavenger is preferably 0.1 to 20,000 parts by mass, and more preferably 0.6 to 5,000 parts by mass, per 100 parts by mass of the photoacid generator.

The coloration inhibitor can use the conventional coloration inhibitors, and an antioxidant is generally effective. Examples of the coloration inhibitor include a phenol-based antioxidant {such as monophenol-based, bisphenol-based or polyphenol-based}, a sulfur-based antioxidant and a phosphorus-based antioxidant.

When the photosensitive composition contains the coloration inhibitor, the content of the coloration inhibitor is preferably 0.1 to 20,000 parts by mass, and more preferably 0.6 to 5,000 parts by mass, per 100 parts by mass of the photoacid generator.

The solvent is not particularly limited so long as it can be used for dissolution of the cationically polymerizable compound and for viscosity control of the photosensitive composition. Examples of the solvent include an ether {such as anisol, diethyl ether, tetrahydrofuran, 1,4-dioxane or ethyl-tert-butyl ether}; an aromatic hydrocarbon {such as toluene, xylene, cumene, ethylbenzene or mesitylene}; a ketone {such as acetone, methyl ethyl ketone, isobutyl ketone or cyclohexanone}: an alcohol {such as methanol, ethanol, isopropyl alcohol or tert-butanol}; and a nitrile {such as acetonitrile}.

When the photosensitive composition contains the solvent, the content of the solvent is preferably 50 to 2,000,000 parts by mass, and more preferably 200 to 500,000 parts by mass, per 100 parts by mass of the photoacid generator.

Examples of the non-reactive resin include polyester, polyvinyl acetate, polyvinyl chloride, polybutadiene, polycarbonate, polystyrene, polyvinyl ether, polyvinyl butyral, polybutene, a hydrogenated product of a styrene-butadiene block copolymer, a copolymer of (meth)acrylic ester, and polyurethane. The number average molecular weight of those resins is preferably 1,000 to 500,000, and more preferably 5,000 to 100,000 (the number average molecular weight is a value measured by the general method such as GPC).

When the photosensitive composition contains the non-reactive resin, the content of the non-reactive resin is preferably 5 to 400,000 parts by mass, and more preferably 50 to 150,000 parts by mass, per 100 parts by mass of the photoacid generator.

When the non-reactive resin is contained, the non-reactive resin is desirably dissolved in the solvent to facilitate dissolution of the non-reactive resin in the cationically polymerizable compound and the like.

The radically polymerizable compound can use the conventional radically polymerizable compounds {such as The Technical Association of Photopolymers, Japan "PHOTOPOLYMER HANDBOOK" (1989, Kogyo Chosakai Publishing Co., Ltd.), General Technical Center "Technology of UV.EB Curing" (1982, General Technical Center), Rad Tech Japan "UV.EB Curing Material" (1992, CMC), and Technical Information Institute Co., Ltd. "Insufficient Curing.Inhibition Factor in UV Curing and Its Countermeasure" (2003, Technical Information Institute Co., Ltd.)}, and examples thereof include a monofunctional monomer, a bifunctional monomer, a polyfunctional monomer, epoxy (meth)acrylate, polyester (meth)acrylate and urethane (meth)acrylate.

Examples of the monofunctional monomer include methyl (meth)acrylate, ethyl (meth)acrylate, 2-ethylhexyl (meth)acrylate, lauryl (meth)acrylate, 2-hydroxyethyl (meth)acrylate, 1,6-hexanediol mono(meth)acrylate, styrene, vinyl cyclohexene, isobutylene and butadiene.

Examples of the bifunctional monomer include di(meth) acrylates of dihydric alcohols or alkylene oxide adducts of those {such as di(meth)acrylates of dihydric alcohols (such as ethylene glycol, propylene glycol, bisphenol A, hydrogenated product of bisphenol A, and alkylene oxide adducts of those)}, and divinylbenzene.

The polyfunctional monomer can use monomers other than the bifunctional monomer, and examples thereof include (meth)acrylates of polyhydric alcohols (such as trimethylolpropane, glycerin, pentaerythritol and alkylene oxide adduct of pentaerythritol).

Examples of the epoxy (meth)acrylate include epoxy (meth)acrylates obtained by reacting epoxides {such as aromatic epoxide, alicyclic epoxide and aliphatic epoxide} with (meth)acrylic acid.

Examples of the polyester (meth)acrylate include polyester (meth)acrylates obtained by esterifying hydroxy-terminated polyester obtained from aromatic polybasic acid {such as phthalic acid, isophthalic acid, terephthalic acid, trimellitic acid and pyromellitic acid} or aliphatic polybasic acid {such as succinic acid, adipic acid or an sebasic acid} and polyhydric alcohol {such as ethylene glycol, diethylene glycol, polyethylene glycol, propylene glycol, dipropylene glycol, polypropylene glycol, neopentyl glycol, polytetramethylene glycol, 1,3-butanediol, 1,4-butanediol, 1,6-hexanediol, trimethylolpropane, glycerin, pentaerythritol, bisphenol or their alkylene oxide adducts}, with (meth)acrylic acid.

Examples of the urethane (meth)acrylate include urethane (meth)acrylates obtained by a urethane reaction between an isocyanate-terminated prepolymer obtained from polyfunctional isocyante {such as alicyclic isocyanate (such as isophorone diisocyanate or dicyclohexylmethane diisocyanate), aliphatic isocyanate (such as tetramethylene diisocyanate or hexamethylene diisocyanate) and aromatic isocyanate (such as toluene diisocyanate, phenylene diisocyanate or diphenylmethane diisocyanate)} and polyhydric alcohol {such as ethylene glycol, diethylene glycol, polyethylene glycol, propylene glycol, polypropylene glycol, neopentyl glycol, polytetramethylene glycol, 1,3-butanediol, 1,4-butanediol, 1,6-hexanediol, trimethylolpropane, glycerin, pentaerythritol, bisphenol, hydrogenated bisphenol, polycaprolactone diol, polyester diol or polycarbonate doil}, and hydroxy-containing (meth)acryate {such as 2-hydroxymethyl (meth)acrylate, 2-hydroxypropyl (meth)acrylate, 4-hydroxybutyl (meth)acrylate or tri(meth)acrylate of pentaerythritol}.

When the photosensitive composition contains the radically polymerizable compound, the content of the radically polymerizable compound is preferably 5 to 400,000 parts by mass, and more preferably 50 to 150,000 parts by mass, per 100 parts by mass of the photoacid generator.

When the photosensitive composition contains the radically polymerizable compound, a radical polymerization initiator initiating a polymerization by heat or light is preferably used to highly polymerize the radically polymerizable compound.

The radical polymerization initiator can use the conventional radical polymerization initiators, and examples thereof include a thermoradical polymerization initiator and a photoradical polymerization initiator.

Examples of the thermoradical polymerization initiator include an organic peroxide {such as ketone peroxide (such as methyl ethyl ketone peroxide or cyclohexanone peroxide), peroxyketal (such as 2,2-bis(tert-butylperoxy)butane or 1,1-bis(tert-butylperoxy)cyclohexane), hydroxyperoxide (such as tert-butyl hydroxyperoxide or cumene hydroperoxide), dialkyl peroxide (such as di-tert-butyl peroxide), diacyl peroxide (such as isobutylyl peroxide, lauroyl peroxide or benzoyl peroxide), peroxy dicarbonate (such as diisopropylperoxy carbonate), peroxy ester (such as tert-butylperoxy isobutylate or 2,5-dimethyl-2,5-di(benzoylperoxy)hexane)}, and an azo compound {such as 1,1'-azobis(cyclohexane-1-carbonitrile), 2,2'-azobisisobutyronitrile, 2,2'-azobis(2,4-dimethyl-4-methoxyvaleronitrile), 2,2'-azobis(2-methylpropioneamidine)dihydrochloride, 2,2'-azobis[2-methyl-N-(2-propenyl)propioneamidine]dihydro chloride, 2,2'-azobis(2-methylpropioneamide), 2,2'-azobis[2-methyl-N-(2-hydroxyethyl)propioneamide], 2,2'-azobis(2-methylpropane), 2,2'-azobis(2,4,4-trimethylpentane) or dimethyl-2,2'-azobis(2-methylpropionate)}.

Examples of the photoradical polymerization initiator include an acetophenone initiator {such as acetophenone, p-tert-butyltrichloroacetophenone or 2,2-diethoxyacetophenone}, a benzophenone initiator {such as benzophenone, methyl o-benzoylbenzoate or 4-benzoyl-4'-methyldiphenylsulfide}, Michler's ketone initiator {such as 4,4'-bis(dimethylamino)benzophenone or 4,4'-bis(diethylamino)benzophenone}, a benzoin initiator {such as benzoin or benzoin methyl ether}, a thioxanthone initiator {such as thioxanthone, 2-methylthioxanthone, 2-ethylthioxanthone, 2-chlorothioxanthone, 2-isopropylthioxanthone or 2,4-diethylthioxanthone}, and an acyl phosphine initiator {such as monoacylphosphine oxide or bisacylphosphine oxide}.

When the photosensitive composition contains the radical polymerization initiator, the content of the radical polymerization initiator is preferably 0.01 to 20 parts by mass, and more preferably 0.1 to 10 parts by mass, per 100 parts by mass of the radically polymerizable compound.

When the photosensitive composition of the present invention contains the photoacid generator including the sulfonium salt of the present invention, and the cationically polymerizable compound, the photosensitive composition can be prepared by uniformly mixing and dissolving the photoacid generator, the cationically polymerizable compound, and as necessary, additives at room temperature (about 20 to 30° C.) or as necessary, under heating (about 40 to 90° C.), or further kneading the resulting mixture by three rolls or the like.

When the photosensitive composition of the present invention contains the cationically polymerizable compound, the composition is cured by irradiation with energy rays, thereby obtaining a cured product. The energy rays may be any energy rays so long as it has energy inducing decomposition of the sulfonium salt of the present invention, but are preferably energy rays of ultraviolet to visible light region (wavelength: about 100 to 800 nm) obtained from a low pressure, medium pressure, high pressure or ultra-high pressure mercury vapor lamp, a metal halide lamp, an LED lamp, a xenon lamp, a carbon arc lamp, a fluorescent lamp, semiconductor solid laser, argon laser, He—Cd laser, KrF excimer laser, ArF excimer laser or $F_2$ laser. The energy rays can use electron beams or radiations having high energy such as X-rays.

The irradiation time of energy rays is influenced by intensity of energy rays and permeability of energy rays to the photosensitive composition, but is sufficient to be about 0.1 to 10 seconds at ordinary temperatures (about 20 to 30° C.). However, where the transmission properties of energy rays are low or the photosensitive composition has large thickness, it may be preferred to increase the irradiation time. Almost all photosensitive compositions cure in 0.1 second to several minutes after irradiation with energy rays by cation polymerization. If necessary, it is possible to after-cure the cured product by heating at room temperature (about 20 to 30° C.) to 150° C. for several seconds to several hours after irradiation with energy rays.

Examples of the specific uses of the photosensitive composition of the present invention include a paint, a coating material, an ink, an ink-jet ink, a positive-type resist, a resist film, a liquid resist, a negative-type resist, an MEMS resist, a photosensitive material, various adhesives, a molding material, a casting material, a putty, a glass fiber impregnant, a filler, a sealing material, an encapsulant, an optical semiconductor (LED) encapsulant, a nanoimprint material, an optical shaping material and a micro-optical shaping material.

The sulfonium salt of the present invention produces strong acid when irradiated with light, and therefore can be used as the photoacid generator for the conventional chemically amplified resist material (Japanese Unexamined Patent Application, Publication Nos. 2003-267968, 2003-261529, and 2002-193925 and the like).

The chemically amplified resist material includes (1) two-component system chemically amplified positive-type resist including a resin becoming soluble in an alkali developing solution under the action of an acid, and a photoacid generator as essential components, (2) three-component system chemically amplified positive-type resist including a resin soluble in an alkali developing solution, a dissolution inhibitor becoming soluble in an alkali developing solution under the action of an acid, and a photoacid generator, as essential components, and (3) chemically amplified negative-type resist including a resin soluble in an alkali developing solution, a crosslinking agent crosslinking the resin by the heat treatment in the presence of an acid, thereby making the resin insoluble in the alkali developing solution, and a photoacid generator, as essential components. Anion of the sulfonium salt of the present invention used as the photoacid generator in (1) and (2) is preferably anions represented by "MY$_a^-$" and "R$^{x2}$SO$_3^-$" described before.

The resin becoming soluble in an alkali developing solution under the action of an acid in (1) is described below. The resin soluble in an alkali developing solution in (2) and (3) is a resin in the state that the resin becoming soluble in an alkali developing solution under the action of an acid is not protected by a protective group, and is appropriately selected from a polymer (acryl resin) of a monomer having an unsaturated double bond, including an unsaturated carboxylic acid such as (meth)acrylic acid, a polymer (polyhydroxystyrene resin) of a monomer having an unsaturated double bond, including hydroxystyrenes, a novolak resin obtained by condensation of phenols, and the like.

Resin becoming soluble in alkali developing solution under action of acid in (1)

The resin becoming soluble in an alkali developing solution under the action of an acid in (1) (hereinafter referred to as "resin (1)") is not particularly limited so long as it is a resin having an acidic group protected by a protective group. The acidic group is not particularly limited so long as it is a group showing acidity by the definition of Broensted. Examples of the preferred acidic group include a carboxyl group and a phenolic hydroxyl group.

Preferred examples of the resin (1) in the state of not being protected by a protective group include a polymer (acryl resin) of a monomer containing an unsaturated double bond, including an unsaturated carboxylic acid such as (meth)acrylic acid, a polymer (polyhydroxystyrene resin) of a monomer having an unsaturated double bond, including hydroxystyrenes, and a novolak resin obtained by condensation of phenols.

Basic skeleton of the resin (1) is not limited to the basic skeletons of those resins.

Novolak resin, hydroxystyrene resin and acryl resin that are preferably used as the resin (1) are respectively described below.

The resin (1) may be prepared using a monomer protected by a protective group, and may be prepared by protecting at least a part of acidic groups in the resin having acidic groups with a protective group according to the conventional method. When the resin (1) is an acryl resin or a polyhydrostyrene resin, the resin (1) is preferably produced by polymerizing a monomer containing unsaturated carboxylic acid protected with a protective group.

Examples of the unsaturated carboxylic acid include a monocarboxylic acid such as (meth)acrylic acid or crotonic acid; and a dicarboxylic acid such as maleic acid, fumaric acid, citraconic acid, mesaconic acid or itaconic acid. Of those unsaturated carboxylic acids, (meth)acrylic acid is preferred.

The protective group is not particularly limited so long as it is used as a protective group of an acidic group in a resin conventionally used in a photosensitive composition. Groups represented by the following formulae (g1), (g2) and (g3), a vinyloxyethyl group and a trialkylsilyl group are preferred.

[Chemical formula 11]

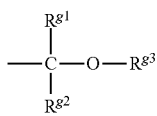

(g1)

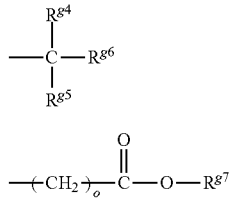

In the formula (g1), R$^{g1}$ represents hydrogen atom or a hydrocarbon group having 1 to 20 carbon atoms that may be discontinued by —O— or —S—, R$^{g2}$ and R$^{g3}$ each independently represent a hydrocarbon group having 1 to 20 carbon atoms that may be discontinued by —O— or —S—, R$^{g1}$ and R$^{g2}$ may be combined to form a ring, and R$^{g2}$ and R$^{g3}$ may be combined to form a ring.

In the formula (g2), R$^{g4}$, R$^{g5}$ and R$^{g6}$ each independently represent a linear or branched alkyl group having 1 to 6 carbon atoms, or a linear or branched fluorinated alkyl group having 1 to 10 carbon atoms. Optional two groups in R$^{g4}$, R$^{g5}$ and R$^{g6}$ may be combined to form a ring.

In the formula (g3), R$^{g7}$ represents a linear, branched or cyclic alkyl group having 1 to 6 carbon atoms, and o is 0 or 1.

In the formula (g1), R$^{g1}$, R$^{g2}$ and R$^{g3}$ are a hydrocarbon group having 1 to 20 carbon atoms. The carbon atom number in the hydrocarbon group is preferably 1 to 10, more preferably 1 to 8, and particularly preferably 1 to 6. The hydrocarbon group may be an aliphatic hydrocarbon group, may be an aromatic hydrocarbon group, and may be a combination of an aliphatic hydrocarbon group and an aromatic hydrocarbon group.

When R$^{g1}$, R$^{g2}$ and R$^{g3}$ are an aliphatic hydrocarbon group, the aliphatic hydrocarbon group may be a chain structure, may be a cyclic structure, and may contain a chain structure and a cyclic structure. The aliphatic hydrocarbon group may have an unsaturated bond. The aliphatic hydrocarbon group is preferably a saturated aliphatic hydrocarbon group.

When R$^{g1}$, R$^{g2}$ and R$^{g3}$ are a chain aliphatic hydrocarbon group, examples of the chain aliphatic hydrocarbon group include methyl group, ethyl group, n-propyl group, isopropyl group, n-butyl group, isobutyl group, sec-butyl group, tert-butyl group, n-pentyl group, isopentyl group, tert-pentyl group, n-hexyl group, n-heptyl group, n-octyl group, 2-ethyl-n-hexyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group and n-eicosyl group.

When R$^{g1}$, R$^{g2}$ and R$^{g3}$ are a cyclic aliphatic hydrocarbon group and the cyclic aliphatic hydrocarbon group is a cycloalkyl group, specific examples of the cycloalkyl group include cyclopropyl group, cyclobutyl group, cyclopentyl group, cyclohexyl group, cycloheptyl group, cyclononyl group, cyclodecyl group, cycloundecyl group and cyclododecyl group.

When R$^{g1}$, R$^{g2}$ and R$^{g3}$ are a cyclic aliphatic hydrocarbon group and the cyclic aliphatic hydrocarbon group is a polycyclic group, specific examples of the polycyclic group include groups in which one hydrogen atom has been removed from the following polycyclic aliphatic hydrocarbons.

[Chemical formula 12]

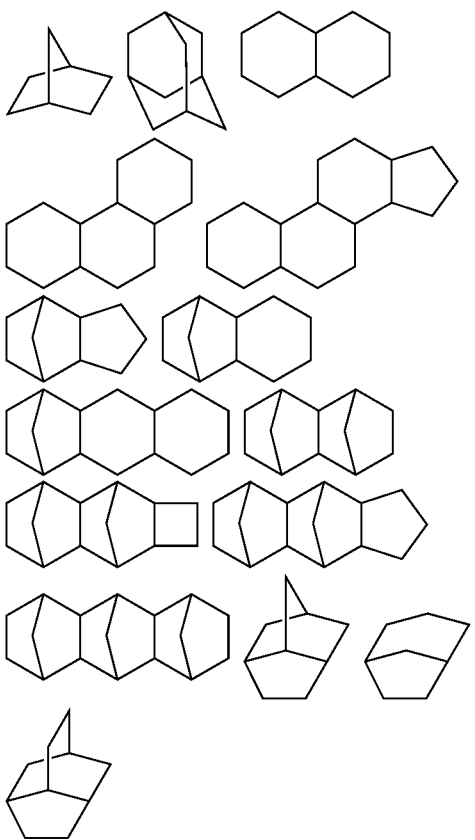

When $R^{g1}$, $R^{g2}$ and $R^{g3}$ are an aromatic hydrocarbon group, examples of the aromatic hydrocarbon group include phenyl group, naphthyl group, anthryl group, biphenylyl group, phenathrenyl group and fluorenyl group.

When $R^{g1}$, $R^{g2}$ and $R^{g3}$ are a group of a combination of an aliphatic hydrocarbon group and an aromatic hydrocarbon group, example of the group includes an aralkyl group. Specific examples of the aralkyl group include benzyl group, phenetyl group, 3-phenyl-n-propyl group, 4-phenyl-n-butyl group, α-naphthylmethyl group, β-naphthylmethyl group, 2-(α-naphthyl)ethyl group and 2-(β-naphthyl)ethyl group.

When $R^{g1}$, $R^{g2}$ and $R^{g3}$ are a hydrocarbon group containing an aromatic ring, the aromatic ring may be substituted with at least one substituent selected from the group consisting of a halogen atom, a hydroxyl group, an alkyl group having 1 to 10 carbon atoms, an alkoxy group having 1 to 10 carbon atoms, an alkanoyl group having 2 to 10 carbon atoms and an alkanoyloxy group having 2 to 10 carbon atoms. When a plurality of substituents are present on the aromatic ring, a plurality of aromatic rings may be the same or different.

In the formula (g1), $R^{g1}$ is preferably hydrogen atom. $R^{g2}$ is preferably methyl group. $R^{g3}$ is preferably ethyl group, isobutyl group, cyclohexyl group, 2-ethyl-n-hexyl group or octadecyl group.

When $R^{g2}$ and $R^{g3}$ are combined to form a ring, the ring is a hetero ring containing oxygen atom bonded to $R^{g3}$. The hetero ring containing oxygen atom has preferably 3 to 7, and more preferably 4 to 6, carbon atoms. The hetero ring may further contain a hetero atom other than the oxygen atom bonded to $R^{g3}$. Examples of the hetero atom in such a case include oxygen atom, sulfur atom and nitrogen atom.

When $R^{g1}$ and $R^{g2}$ are combined to form a ring, the ring is preferably 3 to 12-membered saturated aliphatic hydrocarbon rings. When $R^{g1}$ and $R^{g2}$ are combined to form a 6-membered saturated aliphatic hydrocarbon ring, the group represented by the formula (g1) is a group represented by the following formula. In the formula, $R^{g3}$ is the same as defined in the formula (g1).

[Chemical formula 13]

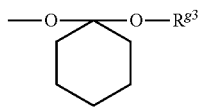

Preferred examples of the group represented by the formula (g1) are shown below.

[Chemical formula 14]

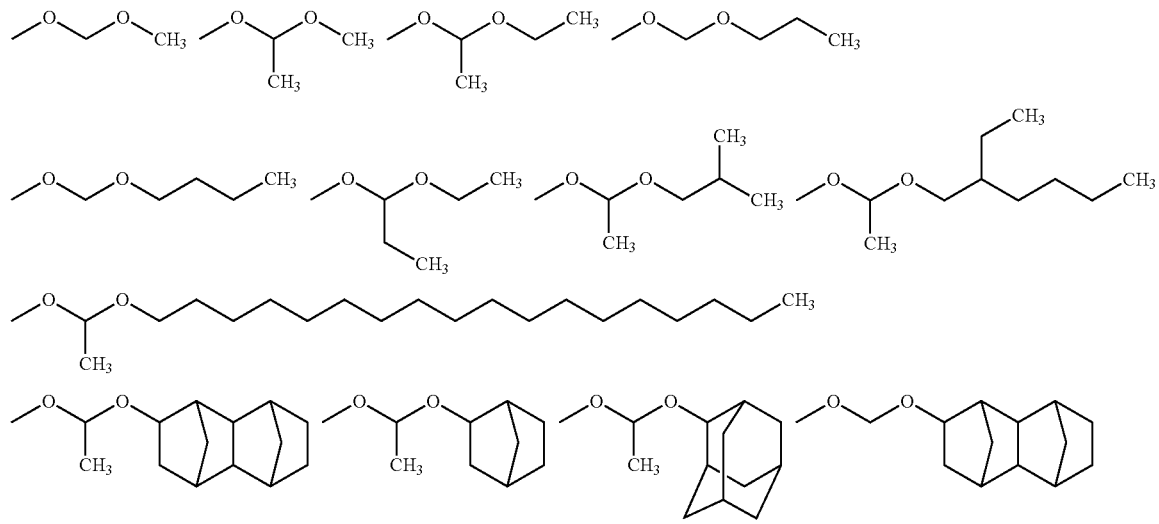

-continued

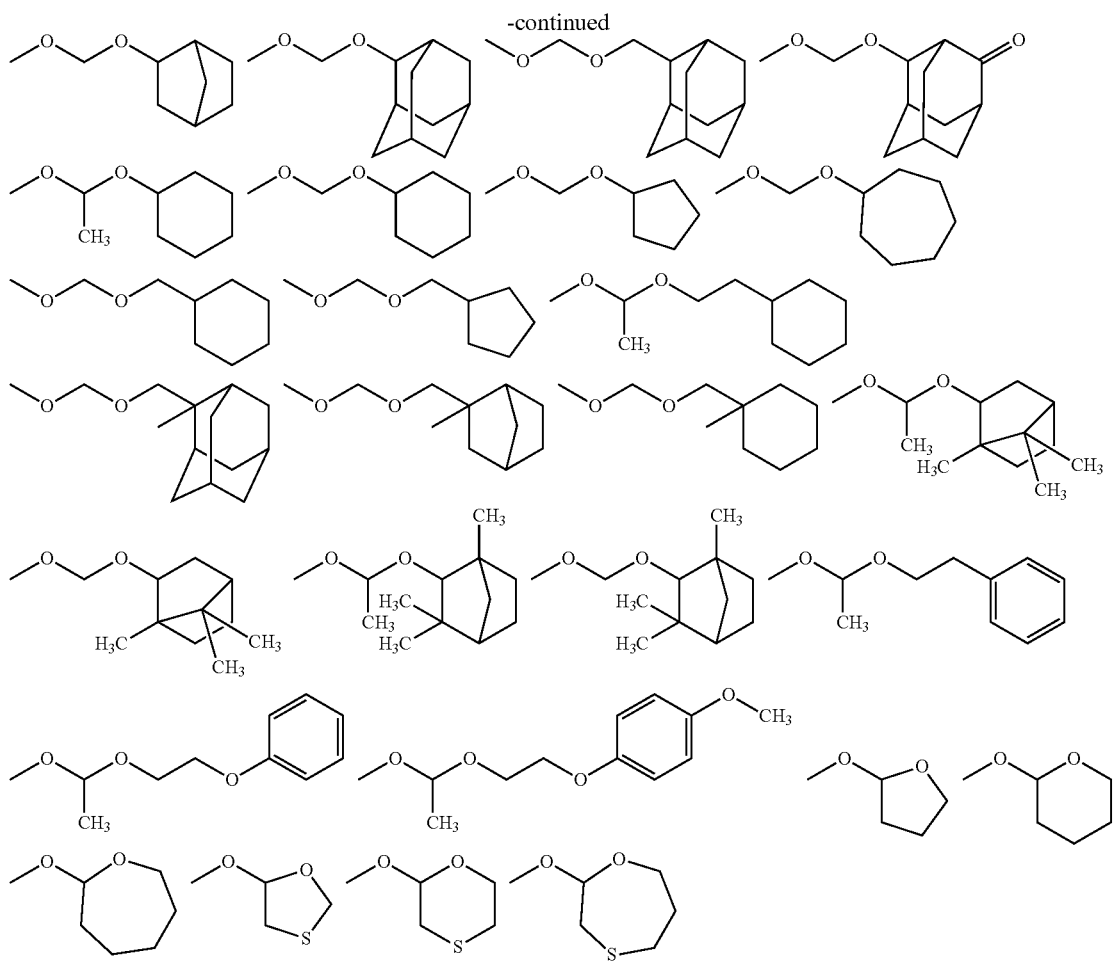

In the formula (g2), when $R^{g4}$, $R^{g5}$ and $R^{g6}$ are an alkyl group, specific examples of the alkyl group include methyl group, ethyl group, n-propyl group, isopropyl group, n-butyl group, isobutyl group, sec-butyl group, tert-butyl group, n-pentyl group, isopentyl group, tert-pentyl group, n-hexyl group, b-heptyl group, n-octyl group, 2-ethyl-n-hexyl group, n-nonyl group and n-decyl group.

In the general formula (g2), when any optional two groups of $R^{g4}$, $R^{g5}$ and $R^{g6}$ are combined to form a ring, the ring is preferably an aliphatic hydrocarbon ring having 5 to 20 carbon atoms. The aliphatic hydrocarbon ring may be monoalkane and may be polycycloalkane such as bicycloalkane, tricycloalkane or tetracycloalkane. Specific examples of the aliphatic hydrocarbon ring include monocycloalkane such as cyclopentane, cyclohexane, cycloheptane or cyclooctane, and polycycloalkane such as adamantane, norbornane, isobornane, tricyclodecane or tetracyclodecane.

The ring formed by combining any optional two groups of $R^{g4}$, $R^{g5}$ and $R^{g6}$ may have a substituent. Examples of the substituent include a polar group such as hydroxyl group, cyano group or oxygen atom (=O), and a linear or branched alkyl group having 1 to 4 carbon atoms. The polar group is particularly preferably oxygen atom (=O).

Preferred examples of the group represented by the formula (g2) include the following groups.

[Chemical formula 15]

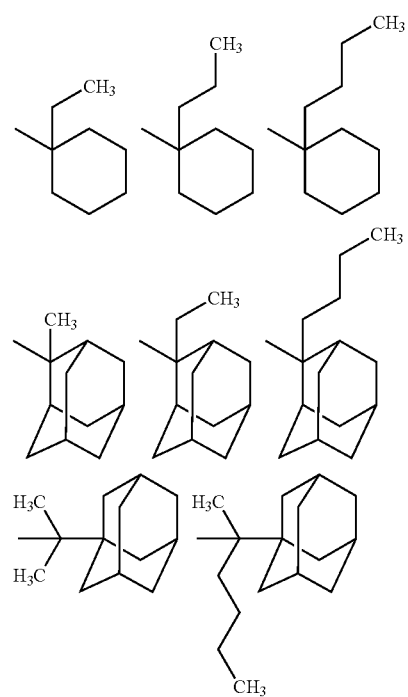

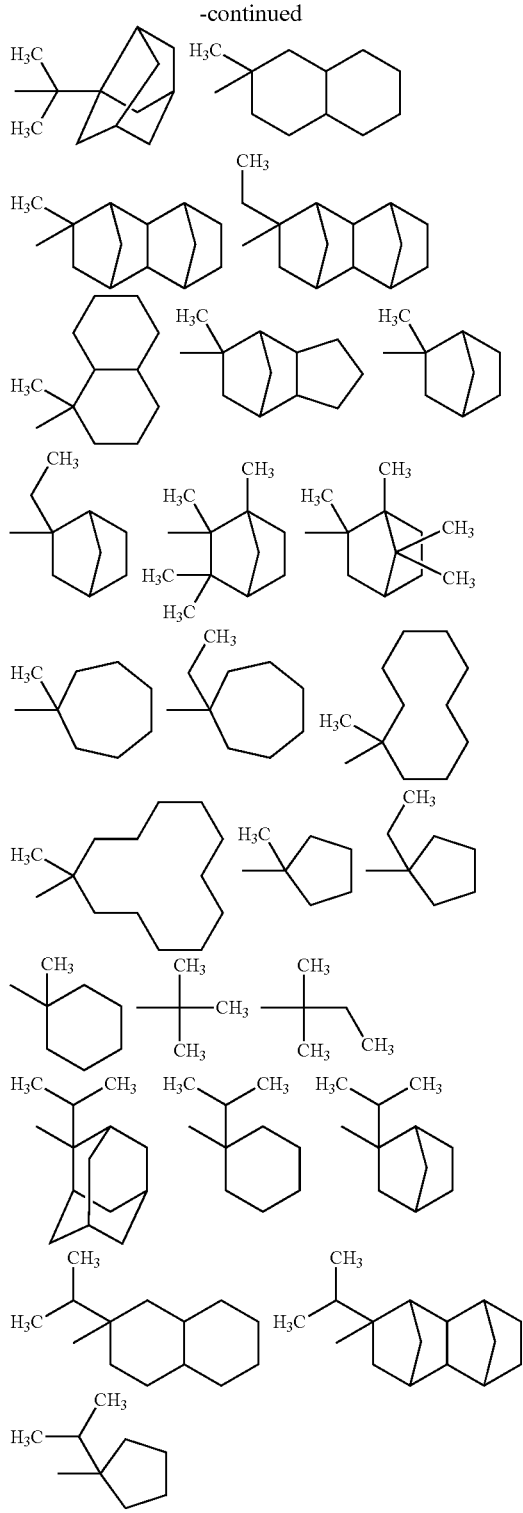

Examples of the protective group represented by the formula (g3) specifically include tert-butoxycarbonyl group and tert-butoxycarbonylmethyl group. Examples of the trialkylsilyl group include groups having 1 to 6 carbon atoms in each alkyl moiety, such as trimethylsilyl group or tri-tert-butyldimethylsilyl group.

The content of structural unit having an acidic group protected by a protective group in the resin (1) is preferably 1 to 85 mass %, more preferably 2 to 80 mass %, and particularly preferably 3 to 75 mass %, based on the mass of the resin (1). When the content of the structural unit having an acidic group protected by a protective group is within the range, a chemically amplified resist material having good developing property is easy to be obtained.

The resin (1) may have a crosslinking group. The crosslinking group is a functional group capable of being thermally crosslinked when post-baking a patterned film formed. Examples of the preferred crosslinking group include an epoxy group, an oxetanyl group and a group having an unsaturated double bond (such as vinyl group or (meth)acryloyl group). Thermal crosslinking occurs between crosslinking groups when post-baked, and as a result, a film having excellent mechanical property and chemical resistance can be formed.

For example, when the resin (1) has a functional group containing active hydrogen atom, such as carboxyl group, hydroxyl group or amino group, a crosslinking group can be introduced in the resin (1) by reacting the functional group containing active hydrogen atom with epichlorohydrin, (meth)acryloyl chloride, (meth)acrylic anhydride, allyl halide or the like according to the conventional methods.

The resin (1) preferably further has alcoholic hydroxyl group and/or cyclic ether group. The cyclic ether group is a group that is not bonded to oxygen atom. The cyclic ether group is a group in which one or two —$CH_2$— in a (poly)cycloalkyl group having 5 or more carbon atoms are substituted with —O—. The cyclic ether group does not contain oxygen atom in an adjacent state. Of the cyclic ether groups, a group that is bonded to an acid group to form a protective group is defined as a protective group, and is not contained in the resin further having a cyclic ether group.

When the resin (1) further has alcoholic hydroxyl group and/or cyclic ether group, the resolution of the chemically amplified resist material is enhanced.

The alcoholic hydroxyl group is preferably present as a group represented by the following formula (g4) in the resin (1). $R^{g12}$ in the formula (g4) is a linear or branched alkylene group having 1 to 20 carbon atoms.

$$—R^{g12}—OH \quad (g4)$$

The cyclic ether group is preferably present as a group represented by the following formula (g5) in the resin (1). In the formula (g5), $R^{g13}$ represents a single bond or a linear or branched alkylene group having 1 to 6 carbon atoms, and $R^{g14}$ represents a 5-membered or more, preferably 5 to 8-membered, cyclic ether ring.

$$—R^{g13}—R^{g14}— \quad (g5)$$

As one example, an alcoholic hydroxyl group or a cyclic ether group can be introduced in the resin (1) by the following method. However, the method of introducing an alcoholic hydroxyl group or a cyclic ether group in the resin (1) is not limited to the following method.

When the resin (1) or the resin (1) in the state that an acidic group is not protected has a phenolic hydroxyl group, the phenolic hydroxyl group is reacted with a halogenated alkanol represented by Hal-$R^{g12}$—OH (Hal represents a halogen atom, and $R^{g12}$ is the same as defined in the formula (g4)) according to the conventional methods to etherify the phenolic hydroxyl group. Thus, the alcoholic hydroxyl group can be introduced in the resin (1). Examples of the halogenated alkanol include 2-chloroethanol, 3-chloro-n-propanol, 4-chloro-n-butanol, 2-bromoethanol, 3-bromo-n-propanol and 4-bromo-n-butanol.

Furthermore, when the phenolic hydroxyl group is reacted with a cyclic ether compound having a halogen atom at the terminal represented by Hal-$R^{g13}$—$R^{g14}$ (Hal represents a halogen atom, and $R^{g13}$ and $R^{g14}$ are the same as defined in the formula (g5)) according to the conventional methods to etherify the phenolic hydroxyl group, the cyclic ether group can be introduced in the resin (1). Example of the cyclic ether compound having a halogen atom at the terminal includes tetrahydrofurfuryl chloride.

When the resin (1) or the resin (1) being in the state that a hydroxyl group is not protected has a carboxyl group, the carboxyl group is reacted with aliphatic glycols represented by OH—$R^{g12}$—OH ($R^{g12}$ is the same as defined in the formula (g4)) according to the conventional methods to conduct esterification, the alcoholic hydroxyl group can be introduced in the resin (1). Examples of the aliphatic glycols include ethylene glycol, propylene glycol, 1,3-propanediol, 1,4-butanediol, 1,5-pentanediol and 1,6-hexanediol.

Furthermore, when the carboxyl group is reacted with a cyclic ether compound having a hydroxyl group at the terminal represented by OH—$R^{g13}$—$R^{g14}$ ($R^{g13}$ and $R^{g14}$ are the same as defined in the formula (g5)) according to the conventional methods to conduct esterification, the cyclic ether group can be introduced in the resin (1). Examples of the cyclic ether compound having a hydroxyl group at the terminal include tetrahydrofurfuryl alcohol, tetrahydro-4H-pyran-4-methanol and tetrahydro-2H-pyran-3-methanol.

When the resin (1) is an acryl resin or a polyhydroxystyrene resin, an alcoholic hydroxyl group or a cyclic ether group can be introduced in the resin (1) by copolymerizing a monomer having an unsaturated double bond and an alcoholic hydroxyl group or a cyclic ether group with the resin (1).

Preferred examples of the compound that can be used as the monomer having an unsaturated double bond and an alcoholic hydroxyl group or a cyclic ether group include compounds represented by the following formulae (h-1) to (h-22). In the formulae (h-1) to (h-22), $R^{g15}$ represents the group represented by the formula (g4) or the group represented by the formula (g5), and $R^{g16}$ represents hydrogen atom or methyl group.

[Chemical formula 16]

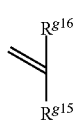

(h-1)

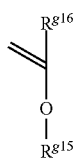

(h-2)

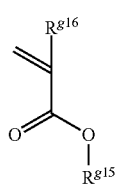

(h-3)

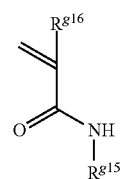

(h-4)

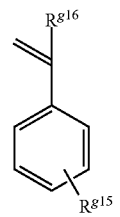

(h-5)

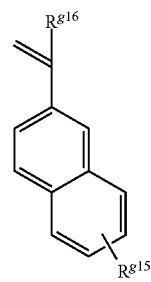

(h-6)

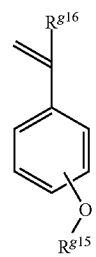

(h-7)

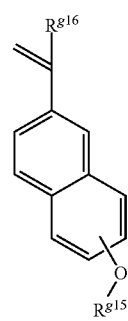

(h-8)

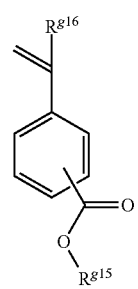

(h-9)

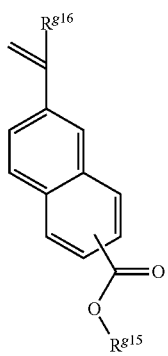
(h-10)
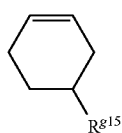
(h-11)
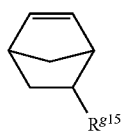
(h-12)
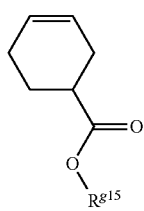
(h-13)
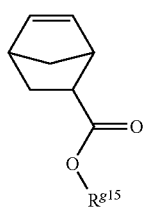
(h-14)
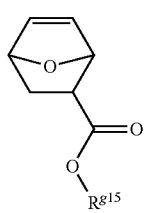
(h-15)
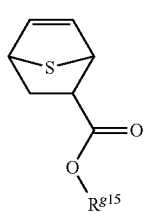
(h-16)
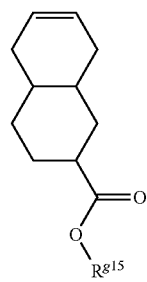
(h-17)
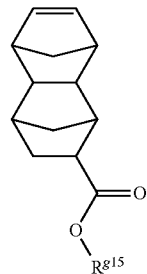
(h-18)
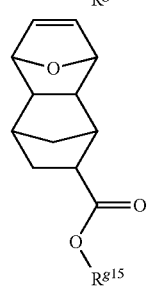
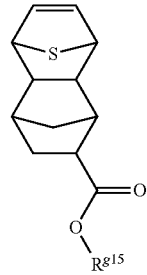
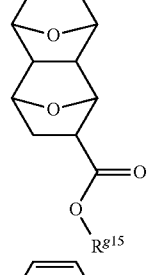
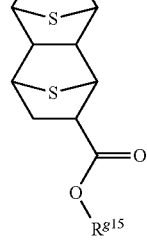

The content of the unit having an alcoholic hydroxyl group and/or a cyclic ether group in the resin (1) is preferably 1 to 30 mass %, and more preferably 2 to 20 mass %, based on the mass of the resin (1). When the resin (1) contains the unit containing an alcoholic hydroxyl group and/or a cyclic ether group in an amount within the range, the resolution of a chemically amplified resist material is satisfactory.

The resin (1) may have a unit containing a lactone-containing cyclic group, a (—$SO_2$—)-containing cyclic group or a carbonate-containing cyclic group.

The "lactone-containing cyclic group" indicates a cyclic group containing a ring (lactone ring) containing —O—C(=O)— in its ring skeleton. The lactone ring is counted as a first ring, and when only the lactone ring is present, the group is called a monocyclic group. When other ring structure is further present, the group is called a polycyclic group regardless of its structure. The lactone-containing cyclic group may be a monocyclic group, and may be a polycyclic group.

The "(—$SO_2$—)-containing cyclic group" indicates a cyclic group containing a ring containing —$SO_2$— in its ring skeleton, and is specifically a cyclic group in which sulfur atom (S) in —$SO_2$— forms a part of a ring skeleton of the cyclic group. The ring containing —$SO_2$— in its ring skeleton is counted as a first ring, and when only the ring is present, the group is called a monocyclic group. When other ring structure is further present, the group is called a polycyclic group regardless of its structure. The (—$SO_2$—)-containing cyclic group may be a monocyclic group, and may be a polycyclic group.

The (—$SO_2$—)-containing cyclic group is particularly preferably a cyclic group containing —O—$SO_2$— in its ring skeleton, that is, a cyclic group containing a sultone ring in which —O—S— in —O—$SO_2$— forms a part of the ring skeleton.

The "carbonate-containing cyclic group" indicates a cyclic group containing a ring (carbonate ring) containing —O—C(=O)—O— in its ring skeleton. The carbonate ring is counted as a first ring, and when only the carbonate ring is present, the group is called a monocyclic group. When other ring structure is further present, the group is called a polycyclic group regardless of its structure. The carbonate-containing cyclic group may be a monocyclic group, and may be a polycyclic group.

The content of the unit having a lactone-containing cyclic group, a (—$SO_2$—)-containing cyclic group or a carbonate-containing cyclic group in the resin (1) is preferably 1 to 80 mass %, and more preferably 2 to 60 mass %, based on the mass of the resin (1). When the resin (1) contains the unit having a lactone-containing cyclic group, a (—$SO_2$—)-containing cyclic group or a carbonate-containing cyclic group in an amount within the range, adhesiveness to a substrate of a chemically amplified resist material is satisfactory.

The resin (1) may have a unit containing a polar group-containing alicyclic skeleton-containing hydrocarbon group.

Example of the alicyclic skeleton-containing hydrocarbon group includes a monocyclic or polycyclic hydrocarbon group having 7 to 15 carbon atoms, and cyclopentane, cyclohexane, adamantane, norbornane, isobornane, tricyclodecane and deteracyclodecane are preferred.

Example of the polar group includes hydroxyl group, a cyano group, a carboxyl group and a hydroxyalkyl group in which a part of hydrogen atoms in an alkyl group has been substituted with fluorine atom, and hydroxyl group is particularly preferred.

The polar group is preferably bonded to secondary or tertiary carbon in the alicyclic skeleton-containing hydrocarbon group. One to three polar groups are preferably bonded to the alicyclic skeleton-containing hydrocarbon group.

The content of the unit containing a polar group-containing alicyclic skeleton-containing hydrocarbon group in the resin (1) is preferably 1 to 80 mass %, and more preferably 2 to 60 mass %, based on the mass of the resin (1). When the resin (1) contains the unit containing a polar group-containing alicyclic skeleton-containing hydrocarbon group in an amount within the range, the resolution of a chemically amplified resist material is satisfactory.

Novolak resin, polyhydroxystyrene resin and acryl resin are described below as preferred examples of the resin (1).

Novolak Resin

Novolak resin is obtained by, for example, addition-condensing an aromatic compound having phenolic hydroxyl group (hereinafter simply referred to as "phenols") and aldehydes in the presence of an acid catalyst.

Examples of the phenols include phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 2,6-xylenol, 3,4-xylenol, 3,5-xylenol, 2,3,5-trimethylphenol, 3,4,5-trimethylphenol, p-phenylphenol, resorcinol, hydroquinone, hydroquinone monomethyl ether, pyogallol, phloroglycinol, hydroxydiphenyl, bisphenol A, gallic acid, gallic ester, α-naphthol and β-nephthol.

Examples of the aldehydes include formaldehyde, furfural, benzaldehyde, nitrobenzaldehyde and acetoaldehyde.

The catalyst used in the addition condensation reaction is not particularly limited. Examples of an acid catalyst used include hydrochloric acid, nitric acid, sulfuric acid, formic acid, oxalic acid and acetic acid.

Flexibility of novolak resin can be further improved by using o-cresol, substituting hydrogen atoms in hydroxyl group in the resin with other substituents, or using bulky aldehydes.

Mass average molecular weight of the novolak resin is not particularly limited so long as it is a range that does not impair the object of the present invention, but is preferably 1,000 to 50,000.

Novolak resin in which at least a part of hydroxyl groups has been protected by a protective group is used as the resin (1). As described before, as necessary a crosslinking group, a carboxyl group bonded to an aromatic group, an alcoholic hydroxyl group and a cyclic ether group are introduced in the novolak resin as the rein (1).

Polyhydroxystyrene Resin

The polyhydroxystyrene resin is a polymer of a monomer containing a styrene-based compound. Examples of the hydroxystyrene-based compound constituting the polyhydroxystyrene resin include p-hydroxystyrene, α-methylhydroxystyrene and α-ethylhydroxystyrene.

The polyhydroxystyrene resin is preferably a copolymer of a hydroxystyrene-based compound and a styrene-based compound. Examples of the styrene-based compound constituting the styrene resin include styrene, chlorostyrene, chloromethylstyrene, vinyltoluene and α-methylstyrene.

Mass average molecular weight of the polyhydroxystyrene resin is not particularly limited so long as it is a range that does not impair the object of the present invention, but is preferably 1,000 to 50,000.

Polyhydroxystyrene resin in which at least a part of hydroxyl groups has been protected by a protective group is used as the resin (1). As described before, as necessary a crosslinking group, a carboxyl group bonded to an aromatic group, an alcoholic hydroxyl group and a cyclic ether group are introduced in the polyhydroxystyrene resin as the resin (1).

Acryl Resin

The acryl resin is preferably a resin obtained by copolymerizing (meth) acrylic acid with a monomer having other unsaturated bond. Examples of the monomer copolymerizable with (meth)acrylic acid include unsaturated carboxylic acid other than (meth)acrylic acid, (meth)acrylic esters, (meth)acrylamides, allyl compound, vinyl ethers, vinyl esters and styrenes.

Preferred examples of the unsaturated carboxylic acid other than (meth)acrylic acid include a monocarboxylic acid such as crotonic acid; and a dicarboxylic acid such as maleic acid, fumaric acid, citraconic acid, mesaconic acid or itaconic acid.

Examples of the (meth)acrylic esters include a linear or branched alkyl (meth)acrylate such as methyl (meth)acrylate, ethyl (meth)acrylate, propyl (meth)acrylate, amyl (meth)acrylate or t-octyl (meth)acrylate; chloroethyl (meth)acrylate, 2,2-dimethylhydroxypropyl (meth)acrylate, 2-hydroxyethyl (meth)acrylate, trimethylolpropanemono (meth)acrylate, benzyl (meth)acrylate, furfuryl (meth) acrylate, tetrahydrofurfuryl (meth)acrylate, and phenyl (meth)acrylate.

Of (meth) acrylic esters that do not have an epoxy group, (meth)acrylic ester having a group having an alicyclic skeleton is preferred.

In the (meth)acrylic ester having a group having an alicyclic skeleton, an alicyclic group constituting the alicyclic skeleton may be a monocyclic group and may be a polycyclic group. Examples of the monocyclic alicyclic group include cyclopentyl group and cyclohexyl group. Examples of the polycyclic alicyclic group include norbornyl group, isobornyl group, tricyclononyl group, tricyclodecyl group and tetracyclododecyl group.

Examples of the (meth)acrylic esters having a group having an alicyclic skeleton include compounds represented by the following formulae (g-16) to (g-23). Of those compounds, compounds represented by the formulae (g-18) to (g-23) are preferred, and the compound represented by the formula (g-18) or (g-19) is more preferred.

[Chemical formula 17]

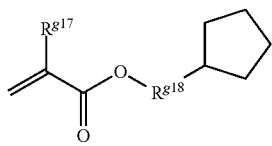
(g-16)

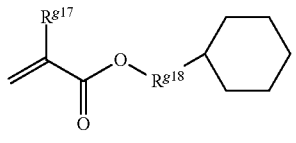
(g-17)

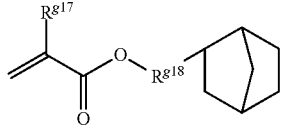
(g-18)

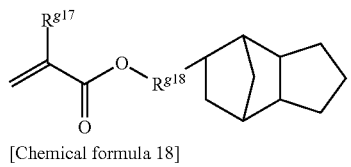
(g-19)

[Chemical formula 18]

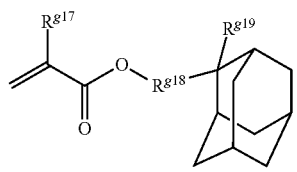
(g-20)

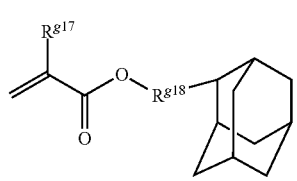
(g-21)

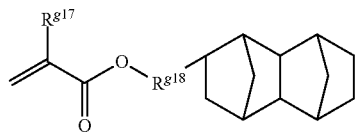
(g-22)

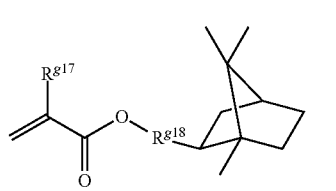
(g-23)

In the above formulae, $R^{g17}$ represents hydrogen atom or methyl group, $R^{g18}$ represents a single bond or a divalent aliphatic saturated hydrocarbon group having 1 to 6 carbon atoms, and $R^{g19}$ represents hydrogen atom or an alkyl group having 1 to 5 carbon atoms. $R^{g18}$ is preferably a single bond or a linear or branched alkylene group such as methylene group, ethylene group, propylene group, tetramethylene group, ethylethylene group, pentamethylene group or hexamethylene group. $R^{g19}$ is preferably methyl group or ethyl group.

Examples of the (meth)acrylamides include (meth)acrylamide, —N-alkyl (meth)acrylamide, —N-aryl (meth)acrylamide, N,N-dialkyl (meth)acrylamide, N,N-aryl (meth) acrylamide, N-methyl-N-phenyl (meth) acrylamide, and N-hydroxyethyl-N-methyl (meth)acrylamide.

Examples of the allyl compound include allyl esters such as allyl acetate, allyl caproate, allyl caprylate, allyl laurate, allyl palmitate, allyl stearate, allyl benzoate, allyl acetoacetate and allyl lactate; and allyloxyethanol.

Examples of the vinyl ethers include an alkyl vinyl ether such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether or tetrahydrofurfuryl vinyl ether; and a vinyl aryl ether such as vinyl phenyl ether, vinyl tolyl ether, vinyl chlorophenyl ether, vinyl-2,4-dichlorophenyl ether, vinyl naphthyl ether or vinyl anthranyl ether.

Examples of the vinyl esters include vinyl butyrate, vinyl isobutyrate, vinyl trimethyl acetate, vinyl diethyl acetate, vinyl valate, vinyl caproate, vinyl chloroacetate, vinyl dichloroacetate, vinyl methoxyacetate, vinyl butoxyacetate, vinyl phenyl acetate, vinyl acetoacetate, vinyl lactate, vinyl-β-phenyl butyrate, vinyl benzoate, vinyl salicylate, vinyl chlorobenzoate, vinyl tetrachlorobenzoate and vinyl naphthoate.

Examples of the styrenes include styrene; alkyl styrene such as methylstyrene, dimethylstyrene, trimethylstyrene, ethylstyrene, diethylstyrene, ispropylstyrene, butylstyrene, hexylstyrene, cyclohexylstyrene, decylstyrene, benzylstyrene, chloromethylstyrene, trifluoromethylstyrene, ethoxymethylstyrene or acetoxymethylstyrene; alkoxystyrene such as methoxystyrene, 4-methoxy-3-methylstyrene or dimethoxystyrene; and halostyrene such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene or 4-fluoro-3-trifluoromethylstyrene.

Acrylic resin in which at least a part of carboxyl groups has been protected by a protective group is used as the resin (1). As described before, as necessary a crosslinking group, a carboxyl group bonded to an aromatic group, an alcoholic hydroxyl group and a cyclic ether group are introduced in the acryl resin as the resin (1).

The total of the amount of the unit having a carboxyl group protected by a protective group and the amount of the unit having a carboxyl group in the acryl resin used as the resin (1) is preferably 1 to 85 mass %, and more preferably 1 to 30 mass %, based on the mass of the resin (1).

The content of the resin (1) in the chemically amplified resist material of (1) above is preferably 50 to 90 mass %, and more preferably 60 to 80 mass %, based on the mass of the solid content of the chemically amplified resist material.

The chemically amplified resist materials of (1) to (3) above may contain a photoacid generator other than the sulfonium salt of the present invention.

The photoacid generator other than the sulfonium salt of the present invention (hereinafter referred to as "other photoacid generator component") is not particularly limited, and materials conventionally proposed as acid generators for a chemically amplified resist can be used.

Examples of the other photoacid generator component include an onium salt-based acid generator such as iodonium salt or sulfonium salt, an oxime sulfonate-based acid generator, a diazomethane-based acid generator such as bisalkyl- or bisarylsulfonium diazomethanes or poly(bissulfonyl)diazomethanes, a nitrobenzylsulonate-based acid generator, an iminosulfonate-based acid generator and a disulfone-based acid generator.

The other photoacid generator component may be used in one kind alone or as mixtures of two or more kinds thereof.

The content of the photoacid generator contained in the chemically amplified resist materials of (1) to (3) above is, for example, 0.1 to 60 mass %, preferably 0.3 to 50 mass %, and more preferably 3 to 40 mass %, based on the mass of the solid content of the chemically amplified resist material. When the photoacid generator is contained in an amount of the above range, the chemically amplified resist material has excellent lithography properties.

When the photoacid generator contained in the chemically amplified resist materials of (1) to (3) above contains the sulfonium salt of the present invention and other photoacid generator component, the proportion of the sulfonium salt of the present invention to the other photoacid generator component is, for example, 0.1 to 99 mass %, preferably 1 to 90 mass %, and more preferably 10 to 70 mass %.

The chemically amplified resist materials of (1) to (3) above preferably contain an organic solvent.

Examples of the organic solvent include a polar solvent such as a ketone-based solvent, an ester-based solvent, an alcohol-based solvent, an ether-based solvent or an amide-based solvent; and a hydrocarbon-based solvent.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methyl cyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate and propyl lactate.

Examples of the alcohol-based solvent include an alcohol such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol; a glycol-based solvent such as ethylene glycol, diethylene glycol or triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethyl butanol.

Examples of the ether-based solvent include the above glycol ether-based solvents, and additionally dioxane and tetrahydrofuran.

Examples of the amide-based solvent include N-methyl-2-pyrrolidone, —N,N-dimethylacetoamide, N,N-dimethylformamide, hexamethylphosphoric triamide, 1,3-dimethyl-2-imidazolidinone, —N,N,N',N'-tetramethylurea and N,N,2-trimethylpropion amide.

Examples of the hydrocarbon-based solvent include an aromatic hydrocarbon-based solvent such as toluene or xylene; and an aliphatic hydrocarbon-based solvent such as pentane, hexane, octane or decane.

The organic solvent may be used in one kind alone or as mixtures of two or more kinds thereof. The content of the solvent in the chemically amplified resist materials of (1) to (3) above is appropriately adjusted depending on a film thickness and the like, and is, for example, 0.5 to 80 mass %, preferably 1 to 60 mass %, and more preferably 2 to 50 mass %, in terms of a solid content concentration.

The chemically amplified resist materials of (1) to (3) above may further contain an acid diffusion control agent component such as a nitrogen-containing compound, an organic acid component, fluorine-based additives, silicon-based additives, a dissolution inhibitor, a surfactant and the like, as necessary.

EXAMPLES

The present invention is further described below by reference to examples, but is not construed as being limited to those examples. Unless otherwise indicated, "parts" means parts by mass, and "%" means mass %".

Synthesis Examples

Synthesis Example 1: Synthesis of Compound 1A

Ethanol (30 mL) and potassium hydroxide (2.1 g, 37 mmol) were placed in a 100 mL round-bottom flask equipped with a stirring bar, and the temperature was set to 0° C. while stirring. Benzene thiol (3.3 g, 30 mmol) and 1-fluoro-2-methyl-4-nitrobenzene (5.6 g, 36 mmol) were added to the flask, and the resulting mixture was stirred overnight at room temperature. After completion of the reaction, saturated aqueous ammonium chloride was added to the flask. An organic layer was separated, and an aqueous layer was extracted with hexane three times. The organic layer obtained was combined with the hexane extract, and the resulting mixture was dried on sodium sulfate, followed by filtration and vacuum concentration. Thus, a crude product was obtained as an oily residue. The crude product was refined by silica gel column chromatography (eluent: hexane). As a result, (2-methyl-4-nitrophenyl)phenyl sulfide was obtained in a yield of 82%.

A mixture of reduced iron (30 g, 540 mmol), ammonium chloride (3.2 g, 30 mmol), isopropanol (200 mL) and water (20 mL) was heated at an outside temperature of 80° C. for 0.5 hour. (2-Methyl-4-nitrophenyl)phenyl sulfide (7.3 g, 30 mmol) was dividedly added to the mixture over 2 hours, following by further heating at 80° C. for 2 hours. The resulting reaction solution was filtered using celite, and the organic solution obtained was concentrated. As a result, the organic solution was solidified. Isopropanol (200 mL) was added to the solidified product to dissolve the solid under reflux, followed by allowing to gradually cool. The solid precipitated was isolated by filtration operation, and then dried. As a result, (2-methyl-4-aminophenyl)phenyl sulfide was obtained in a yield of 98%.

The (2-methyl-4-aminophenyl)phenyl sulfide (6.4 g, 30 mmol) was dissolved in a mixed solution of concentrated sulfuric acid (100 mL) and acetic acid (70 mL). The solution obtained was added dropwise to a solution obtained by mixing concentrated sulfuric acid (30 mL) with sodium nitrate (4.2 g, 60 mmol), under ice cooling. After completion of dropwise addition, the resulting mixture was stirred at room temperature for 1 hour. By this operation, (2-methyl-4-aminophenyl)phenyl sulfide completely disappeared, and (2-methyl-4-diazophenyl)phenyl sulfide was synthesized.

The diazo-form compound-containing sulfuric acid solution prepared above was added dropwise to a solution obtained by mixing copper (I) bromide (60 mmol) with a 48% hydrogen bromide aqueous solution (150 mL) over 2 hours, under ice cooling. The resulting mixture was then heated at an outside temperature of 60° C. for 1 hour, followed by allowing to cool. The solution obtained was added to water (1.5 L), and crystals obtained were collected and dried. As a result, (2-methyl-4-bromophenyl)phenyl sulfide was obtained in a yield of 90%.

A solution obtained by dissolving diphenylsulfoxide (2.4 g, 12 mmol, 1 equivalent) and chlorotrimethylsilane (TM-SCl) (6.5 g, 60 mmol, 5 equivalents) in THF (50 ml) was added to 4-(phenylthio)-3-methylphenyl Grignard reagent (25 mL, 30 mmol, 23 mmol/L, 2.5 equivalents) prepared using the bromo-form prepared above and magnesium as raw materials and using tetrahydrofuran (THF) as a solvent by the conventional method at a temperature of −5° C. to room temperature, and the resulting mixture was then stirred for 30 minutes to conduct a reaction. After completion of the reaction, the reaction liquid obtained was poured in 12% hydrobromic acid (20 mL), and the resulting mixture was extracted with dichloromethane (50 mL) 2 times. The reaction product obtained was cleaned, and then concentrated, dried and crystallized with acetone (50 mL). As a result, 4-(phenylthio)-3-methylphenyldisulfenylsulfonium bromide was obtained in a yield of 76%.

Potassium perfluorobutanesulfonate (9 g, 30 mmol) was added to a dichloromethane solution (50 mL) containing the bromide (14 g, 30 mmol) obtained above, followed by stirring at room temperature for 1 hour. The resulting reaction liquid was added to cold water (150 mL), followed by sufficiently mixing. After still standing, an aqueous layer was removed by a separation funnel, and an organic layer was washed with water (150 mL) 5 times. A solvent was removed by a rotary evaporator under reduced pressure, and a yellow liquid material was obtained. The yellow liquid material was then washed with a toluene/hexane mixed solution to remove impurities, followed by drying at 50° C. under reduced pressure. As a result, 4-(phenylthio)-3-methylphenyldiphenylsulfonium perfluorobutane sulfonate (Compound 1A) was obtained as a yellow viscous material in a yield of 90%.

$^1$H-NMR: d6-dimethylsulfoxide; δ (ppm) 7.7 to 7.9 (12H, m), 7.5 to 7.6 (4H, m), 7.5 (1H, dd), 6.9 to 7.0 (1H, d), 2.4 (3H, s)

[Chemical formula 19]

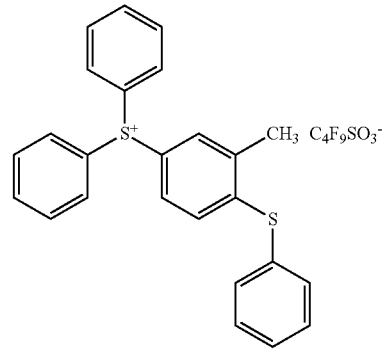

(1A)

Synthesis Example 2: Synthesis of Compound 1B

Transparent 4-(phenylthio)-3-methylphenyldiphenylsulfonium hexafluorophosphate (Compound 1B) was obtained in a yield of 90% in the same manner as in Synthesis Example 1 except that potassium hexafluorophosphate (30 mmol) was used in place of potassium perfluorobutanesulfonate.

$^1$H-NMR: d6-dimethylsulfoxide; δ (ppm) 7.7 to 7.9 (12H, m), 7.5 to 7.6 (4H, m), 7.5 (1H, dd), 6.9 to 7.0 (1H, d), 2.4 (3H, s)

[Chemical formula 20]

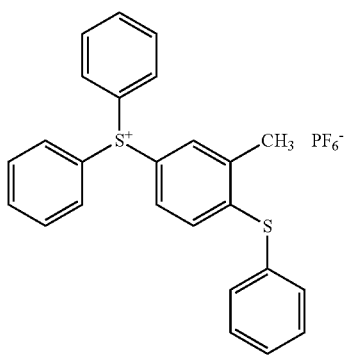

(1B)

Synthesis Example 3: Synthesis of Compound 1C

Dichloromethane solution (50 mL) containing 4-(4-phenylthio)-3-methylphenyldiphenylsulfonium bromide (14 g, 30 mmol) was added dropwise to a suspension obtained by mixing aluminum chloride (2.8 g), acetyl chloride (1.5 g) and dichloromethane (70 mL) under stirring and cooling such that the temperature in the system did not exceed 10° C. After the dropwise addition, the reaction was conducted at room temperature for 2 hours, and the reaction liquid was introduced in cold water (150 mL) under stirring, followed by sufficiently mixing. Potassium perfluorobutanesulfonate (9 g) was then introduced in the reaction mixture, and the resulting mixture was stirred at room temperature for 1 hour and then allowed to stand. An aqueous layer was removed by a separation funnel, and an organic layer was washed with water (150 mL) 5 times, and a solvent was removed by a rotary evaporator under reduced pressure. As a result, a yellow liquid material was obtained. The yellow liquid material was washed with a toluene/hexane mixed solution to remove impurities, and dried at 50° C. under reduced pressure. As a result, 4-(4-acetylphenylthio)-3-methylphenyldiphenyl sulfonium perfluorobutane sulfonate (Compound 1C) was obtained as a yellow viscous material in a yield of 90%.

$^1$H-NMR: d6-dimethylsulfoxide; δ (ppm) 8.0 (2H, d), 7.7 to 7.9 (10H, m), 7.5 to 7.6 (4H, m), 7.5 (1H, dd), 6.9 to 7.0 (1H, d), 2.6 (3H, s), 2.4 (3H, s)

[Chemical formula 21]

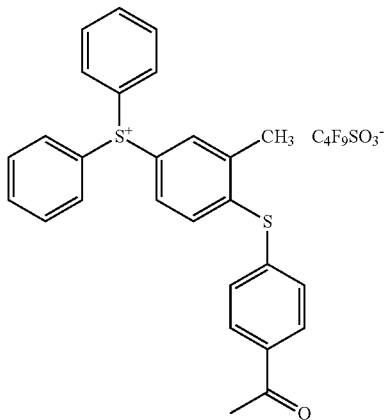

(1C)

Materials

The following materials were used in Examples and Comparative Examples.

Acid Generator

Compound 1A (sulfonium salt of the present invention)

Compound 1B (sulfonium salt of the present invention)

Comparative Compound 1 (conventional sulfonium seat represented by the following formula)

[Chemical formula 22]

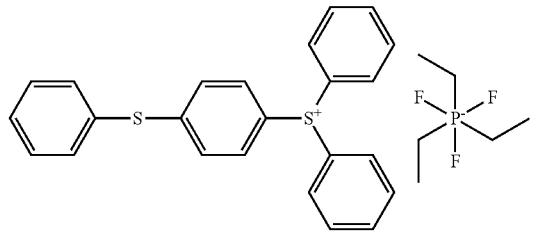

Compounds 2A' to 6A' (onium salts represented by the following formulae 2A' to 6A')

[Chemical formula 23]

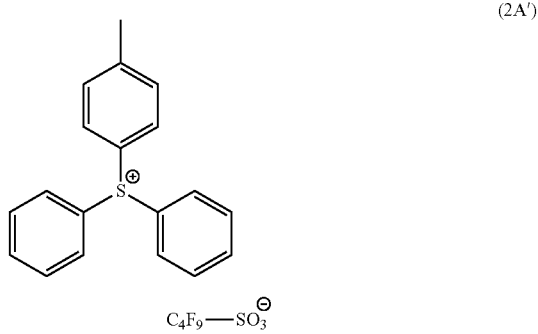

(2A')

(3A')

-continued

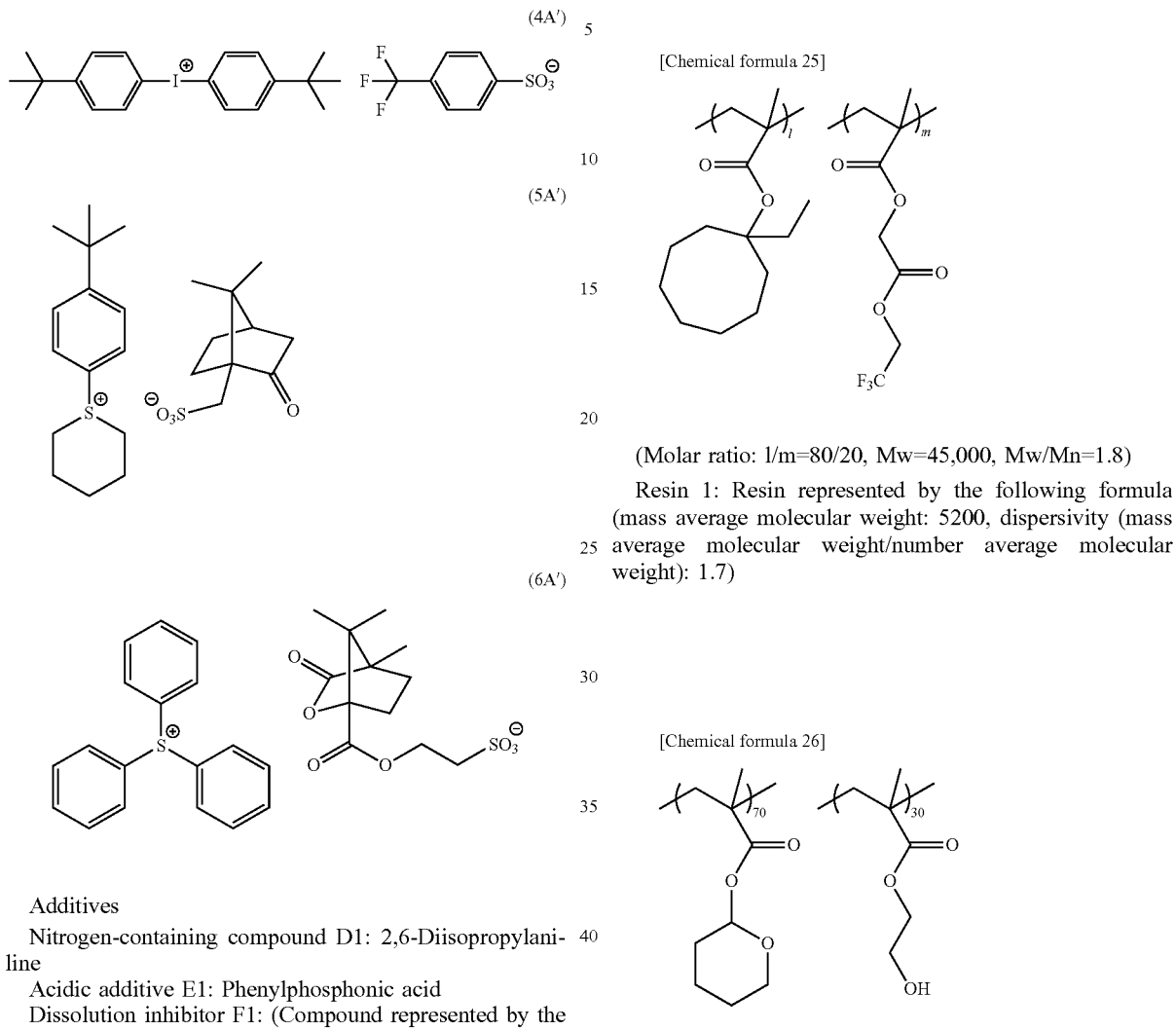

(Molar ratio: l/m=80/20, Mw=45,000, Mw/Mn=1.8)

Resin 1: Resin represented by the following formula (mass average molecular weight: 5200, dispersivity (mass average molecular weight/number average molecular weight): 1.7)

Additives
Nitrogen-containing compound D1: 2,6-Diisopropylaniline
Acidic additive E1: Phenylphosphonic acid
Dissolution inhibitor F1: (Compound represented by the following formula)

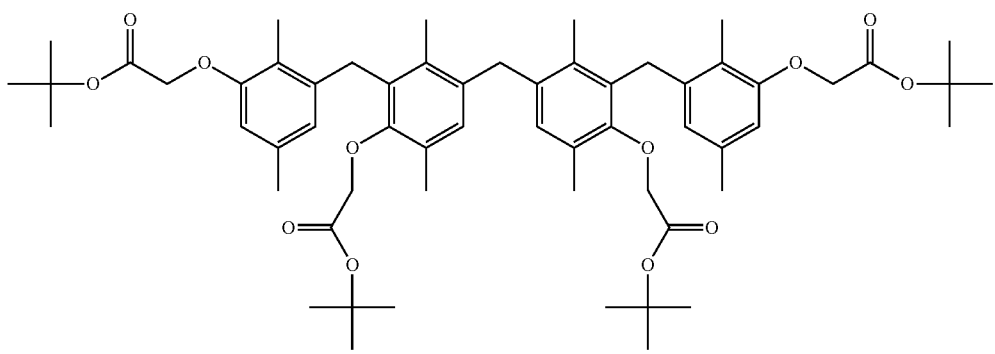

Resin 2: Resin represented by the following formula (mass average molecular weight: 9490, dispersivity: 2)

[Chemical formula 27]

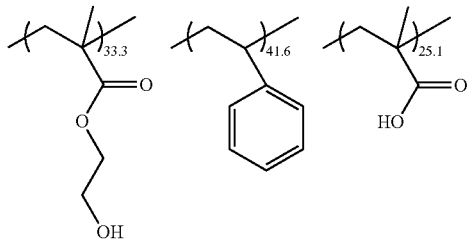

Resin 3: Resin represented by the following formula (mass average molecular weight: 10,000, dispersivity: 1.8)

[Chemical formula 28]

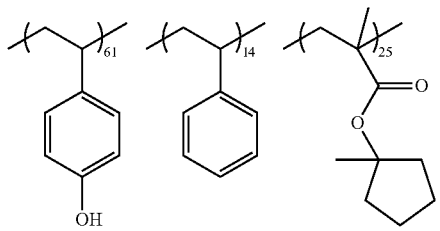

Resin 4: Resin represented by the following formula (mass average molecular weight: 6300, dispersivity: 1.5)

[Chemical formula 29]

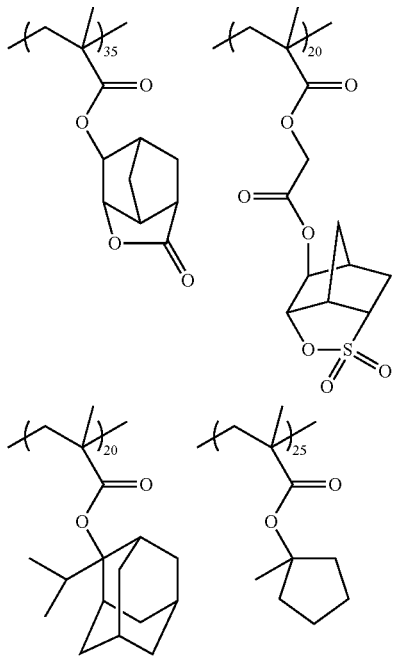

In the above formulae showing Resins 1 to 4, the numerical value attached to each repeating unit is a ratio (mol %) of the mole number of each repeating unit to the mole number of the whole repeating units contained in the respective resins.

Solvent 1: Propylene glycol monomethyl ether acetate

Evaluation of ultraviolet absorption before and after exposure

Example 1

A solution of Compound 1B (solvent: propylene glycol monomethyl ether acetate, concentration: 10%) was applied to a glass substrate using a spin coater, and pre-baked by a hot plate at 80° C. for 120 seconds. Thus, a coated film having a thickness of about 500 nm was formed. The coated film was then irradiated with ultraviolet rays by a high-pressure mercury vapor lamp under the condition of 500 mJ/cm$^2$. Ultraviolet absorption of the coated film before and after exposure was measured using a spectrophotometer. The results are shown in FIG. 1.

Comparative Example 1

Ultraviolet absorption of the coated film before and after exposure was measured in the same manner as in Example 1, except for using Comparative Compound 1 in place of Compound 1B. The results are shown in FIG. 2.

Consideration

As shown in FIG. 2, the tendency was seen that absorption increases in ultraviolet region and longer wavelength region after exposure with ultraviolet rays in the case of Comparative Compound 1. On the other hand, as shown in FIG. 1, in the case of Compound 1B, after exposure with ultraviolet rays, characteristic absorption in the vicinity of 310 nm disappeared, and in addition to this, the absorption decreased in the entire ultraviolet region, or even though the absorption increased, the increased width was very small. Furthermore, the absorption increased in longer wavelength region, but the increased width was very small.

From the above, it is considered that when Comparative Compound 1 was irradiated with ultraviolet rays, a by-product having absorption in an ultraviolet region is formed, this by-product absorbs ultraviolet rays, and ultraviolet rays reaching Comparative Compound 1 decrease. As a result, it is presumed that Comparative Compound 1 is difficult to enhance sensitivity to ultraviolet rays.

On the other hand, it is considered that when Compound 1B was irradiated with ultraviolet rays, a by-product having absorption in an ultraviolet region is difficult to be formed, and ultraviolet rays reaching Compound 1B are difficult to decrease. As a result, it is presumed that Compound B is easy to enhance sensitivity to ultraviolet rays.

Evaluation by $^1$H-NMR

Example 2

The coated film obtained in Example 1 was subjected to $^1$H-NMR measurement before and after exposure. The results are shown in FIG. 3.

Comparative Example 2

The coated film obtained in Comparative Example 1 was subjected to $^1$H-NMR measurement before and after exposure. The results are shown in FIG. 4.

Consideration

As shown in FIG. 3, in the case of Compound 1B, a peak was not observed in a region of about 7.2 to 7.4 ppm corresponding to hydrogen of a benzene ring before exposure, but many peaks were observed after exposure. This suggests that many cleavages of bonding occur by exposure in Compound 1B, and sensitivity to ultraviolet rays is high.

On the other hand, in the case of Comparative Compound 1, a peak was almost not observed in a region of about 7.2 to 7.4 ppm even before exposure and even after exposure as shown in FIG. 4. This suggests that many cleavages of bonding by exposure do not occur in Comparative Compound 1 as compared with Compound 1B, and sensitivity to ultraviolet rays is low.

Evaluation of Sensitivity

Example 3

Resin 1 (70 parts), Resin 2 (30 parts), Compound 1B (0.4 parts) and Solvent 1 were mixed to prepare a positive-type photosensitive composition having a solid content concentration of 25%. The photosensitive composition was applied to a silicon substrate using a spin coater, and pre-baked by a hot plate at 80° C. for 120 seconds to obtain a resin film having a film thickness of about 11.8 μm. The entire surface of the resin film was then irradiated with ultraviolet rays by a high-pressure mercury vapor lamp under the condition of 500 mJ/cm$^2$, and development was conducted with a 2.38% tetramethylammonium hydroxide aqueous solution for 60 seconds. As a result, the resin film was completely dissolved.

Comparative Example 3

Preparation of a positive-type photosensitive composition, preparation of a resin film, irradiation with ultraviolet rays and development were conducted in the same manners as in Example 3, except for using Comparative Compound 1 (0.4 parts) in place of Compound 1B (0.4 parts). As a result, the resin film remained. Even though the exposure amount was changed to 1,000 mJ/cm$^2$, the resin film still remained.

Consideration

As described above, Compound 1B had sensitivity to ultraviolet rays higher than that of Comparative Compound 1. Thus, it was confirmed that the sulfonium salt of the present invention enhances sensitivity to active energy rays as compared with the conventional sulfonium salt.

Evaluation of Pattern Properties by KrF Exposure

Example 4 and Comparative Examples 4 and 5

Each component shown in Table 1 was dissolved in a mixed solvent of propylene glycol monomethyl ether acetate (PGMEA), propylene glycol monomethyl ether (PGME) and ethyl lactate (mass ratio: 50:25;25) as a solvent, and the solid content concentration was adjusted to 6 mass %. Thus, each resist composition was obtained. The numerical values in the brackets with respect to an acid generator and additives in Table 1 are mass ratios to 100 parts by mass of Resin 3, and 1A, 2A' and 3A' are equimolar amounts.

TABLE 1

|  | Resin | Acid generator | | | Additives | | |
|---|---|---|---|---|---|---|---|
| Example 4 | Resin 3 [100] | 1A [2.9] | 4A' [2.6] | 5A' [0.6] | D1 [0.3] | E1 [0.5] | F1 [5.0] |
| Comparative Example 4 | Resin 3 [100] | 2A' [2.4] | 4A' [2.6] | 5A' [0.6] | D1 [0.3] | E1 [0.5] | F1 [5.0] |

TABLE 1-continued

|  | Resin | Acid generator | | | Additives | | |
|---|---|---|---|---|---|---|---|
| Comparative Example 5 | Resin 3 [100] | 3A' [3.0] | 4A' [2.6] | 5A' [0.6] | D1 [0.3] | E1 [0.5] | F1 [5.0] |

Using each resist composition obtained, a resist pattern was formed in the following procedures, and evaluated as follows.

An organic antireflection film composition was applied to a silicon wafer, and dried on a hot plate to form an organic antireflection film having a film thickness of about 130 nm. Each resist composition obtained above was applied to the antireflection film by rotary coating, prebaked (PAB) at 110° C. for 90 seconds on a hot plate, and then dried to form a resist film having a film thickness of about 280 nm.

The resist film was selectively irradiated via a mask with KrF excimer laser (248 nm) by KrF exposure apparatus NSR-S205C (manufactured by Nikon Corporation; NA (numerical aperture)=0.75).

After the exposure, heat (PEB) treatment was performed at 110° C. for 90 seconds, and alkali development was then performed with 2.38 mass % tetramethylammonium hydroxide (TMAH) aqueous solution NMD-3 (trade name, manufactured by Tokyo Ohka Kogyo Co., Ltd.) at 23° C. for 60 seconds to form three kinds of LS patterns having different pitch (isolated line patterns of (1) line width: 120 nm, pitch: 240 nm; (2) trench width: 140 nm, pitch: 560 nm; and (3) line width: 150 nm).

Depth and width of focus (DOF) of each pattern were evaluated. As a result, the resist compositions of Example 4 each had DOF of 200 nm or more, and showed satisfactory properties as compared with Comparative Examples 4 and 5 (the patterns (2) each had DOF of less than 200 nm).

Evaluation of Pattern Properties by ArF Exposure

Example 5 and Comparative Example 6

Each component shown in Table 2 was dissolved in a mixed solvent of propylene glycol monomethyl ether acetate (PGMEA), propylene glycol monomethyl ether (PGME) and cyclohexane (mass ratio: 45:30;25) as a solvent, and the solid content concentration was adjusted to 3 mass %. Thus, each resist composition was obtained. The numerical values in the brackets with respect to an acid generator and additives in Table 2 are mass ratios to 100 parts by mass of Resin 4, and 1A and 2A' are equimolar amounts.

TABLE 2

|  | Resin | Acid generator | Additives |
|---|---|---|---|
| Example 5 | Resin 4 [100] | 1A [7.4] | 6A' [3.7] | G1 [3.0] |
| Comparative Example 6 | Resin 4 [100] | 2A' [5.7] | 6A' [3.7] | G1 [3.0] |

Using each resist composition obtained, a resist pattern was formed in the following procedures, and evaluated as follows.

An organic antireflection film composition was applied to a silicon wafer, and dried on a hot plate to form an organic antireflection film having a film thickness of about 130 nm.

Each resist composition obtained above was applied to the antireflection film using a spinner, prebaked (PAB) at 120°

C. for 60 seconds on a hot plate, and then dried to form a resist film having a film thickness of about 100 nm.

The resist film was selectively irradiated with ArF excimer laser (193 nm) by ArF exposure apparatus NSRX609B (manufactured by Nikon Corporation; NA=1.07).

After the exposure, heat (PEB) treatment was performed at 85° C. for 60 seconds, and alkali development was then performed with 2.38 mass % tetramethylammonium hydroxide (TMAH) aqueous solution NMD-3 (trade name, manufactured by Tokyo Ohka Kogyo Co., Ltd.) at 23° C. for 10 seconds to form two different kinds of isolated patterns ((1) line width: 90 nm, pitch: 2,000 nm; (2) dot width: 80 nm, pitch: 2,000 nm).

The depth and width of focus (DOF) of each pattern was evaluated. As a result, the resist compositions of Example 5 each had DOF of 140 nm or more, and showed satisfactory properties as compared with Comparative Example 6 (the pattern (2) each had DOF of less than 120 nm).

What is claimed is:

1. A sulfonium salt represented by the following general formula (a1):

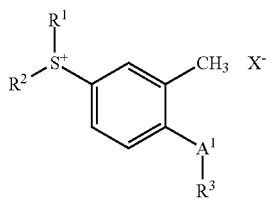

wherein $R^1$ and $R^2$ independently represent an alkyl group which may be substituted with a halogen atom or a group represented by the following general formula (a2), $R^1$ and $R^2$ may be combined to form a ring together with the sulfur atom in the formula, $R^3$ represents a group represented by the following general formula (a3) or a group represented by the following general formula (a4), $A^1$ represents S, O or Se, and $X^-$ represents a monovalent anion, provided that $R^1$ and $R^2$ are not simultaneously an alkyl group which may be substituted with a halogen atom;

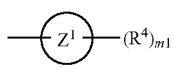

wherein a ring $Z^1$ represents an aromatic hydrocarbon ring, $R^4$ represents an alkyl group which may be substituted with a halogen atom; a hydroxy group, an alkoxy group, an alkylcarbonyl group, an alkoxycarbonyl group, an acyloxy group, an alkylthio group, a thienyl group, a thienylcarbonyl group, a furanyl group, a furanylcarbonyl group, a selenophenyl group, a selenophenylcarbonyl group, a heterocyclic aliphatic hydrocarbon group, an alkylsulfinyl group, an alkylsulfonyl group, a hydroxy(poly)alkyleneoxy group, an amino group which may be substituted, a cyano group, a nitro group or a halogen atom, and m1 is an integer of 0 or more;

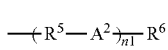

wherein $R^5$ represents an alkylene group which may be substituted with a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, or a group represented by the following general formula (a5), n1 is 0 or 1, when n1 is 0, $R^6$ represents an alkyl group which is substituted with a hydroxy group, an alkoxy group, an alkylcarbonyl group, an arylcarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, or a nitro group, or a group represented by the following general formula (a6'), when n1 is 1, $R^6$ represents an alkyl group which may be substituted with a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy (poly)alkyleneoxy group, an amino group which may be substituted, a cyano group, a nitro group or a halogen atom, or a group represented by the following general formula (a6), and $A^2$ represents, S, O, a sulfinyl group or a carbonyl group;

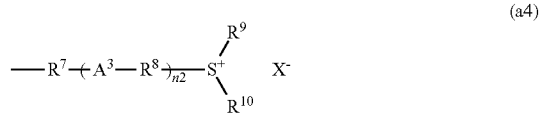

wherein $R^7$ and $R^8$ independently represent an alkylene group which may be substituted with a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy (poly)alkyleneoxy group, an amino group which may be substituted, a cyano group, a nitro group or a halogen atom, or a group represented by the following general formula (a5), $R^9$ and $R^{10}$ independently represent an alkyl group which may be substituted with a halogen atom, or a group represented by the general formula (a2), $R^9$ and $R^{10}$ may be combined to form a ring together with the sulfur atom in the formula, $A^3$ represents a single bond, S, O, a sulfinyl group or a carbonyl group, $X^-$ is the same as defined above, and n2 is 0 or 1, provided that $R^9$ and $R^{10}$ are not simultaneously an alkyl group which may be substituted with a halogen atom;

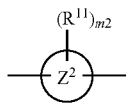
(a5)

wherein a ring $Z^2$ represents an aromatic hydrocarbon ring, $R^{11}$ represents an alkyl group which may be substituted with a halogen atom, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, and m2 is an integer of 0 or more;

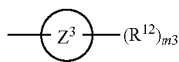
(a6)

wherein a ring $Z^3$ represents an aromatic hydrocarbon ring, $R^{12}$ represents an alkyl group which may be substituted with a halogen atom, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, a thienylcarbonyl group, a furanylcarbonyl group, a selenophenylcarbonyl group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, a nitro group or a halogen atom, and m3 is an integer of 0 or more;

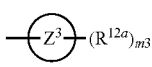
(a6')

wherein a ring $Z^3$ is as stated above, $R^{12a}$ represents a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, a thienylcarbonyl group, a furanylcarbonyl group, a selenophenylcarbonyl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group which may be substituted, a cyano group, or a nitro group, and m3 is an integer of 1 or more.

2. A photoacid generator comprising the sulfonium salt according to claim 1.

3. A photosensitive composition containing a photoacid generator comprising the sulfonium salt according to claim 1, a cationically polymerizable compound, and a solvent.

4. A method of generating an acid, comprising:
applying a photosensitive composition to a substrate, the photosensitive composition containing a photoacid generator comprising the sulfonium salt according to claim 1, a cationically polymerizable compound, and a solvent, and
irradiating the composition with an energy ray to cause the sulfonium salt to generate an acid.

* * * * *